(12) United States Patent
Simpson et al.

(10) Patent No.: US 7,632,661 B2
(45) Date of Patent: Dec. 15, 2009

(54) EXPRESSION ELEMENTS

(75) Inventors: David John Simpson, Staffordshire (GB); Steven Geraint Williams, Cheshire (GB); Alistair Simpson Irvine, Derbyshire (GB)

(73) Assignee: Millipore Corporation, Billerica, MA (US)

( * ) Notice: Subject to any disclaimer, the term of this patent is extended or adjusted under 35 U.S.C. 154(b) by 335 days.

(21) Appl. No.: 11/435,930

(22) Filed: May 17, 2006

(65) Prior Publication Data

US 2008/0097088 A1    Apr. 24, 2008

Related U.S. Application Data

(60) Provisional application No. 60/682,277, filed on May 18, 2005.

(30) Foreign Application Priority Data

May 17, 2005   (GB)   ................. 0509965.0

(51) Int. Cl.
*C12P 21/00*    (2006.01)
*C12N 5/06*     (2006.01)
*C12N 5/10*     (2006.01)
*C12N 5/08*     (2006.01)
*C12N 15/00*    (2006.01)
*C12N 15/11*    (2006.01)
*G01N 33/53*    (2006.01)

(52) U.S. Cl. ................ 435/69.1; 435/7.1; 435/320.1; 435/325; 435/354; 435/358; 435/363; 435/367; 536/24.1

(58) Field of Classification Search ................ None
See application file for complete search history.

(56) References Cited

U.S. PATENT DOCUMENTS

| | | | |
|---|---|---|---|
| 5,583,009 | A | 12/1996 | Palmiter et al. |
| 5,610,053 | A | 3/1997 | Chung et al. |
| 6,063,598 | A | 5/2000 | Enenkel et al. |
| 6,689,606 | B2 | 2/2004 | Antoniou et al. |
| 6,881,556 | B2 | 4/2005 | Antoniou et al. |
| 6,949,361 | B2 | 9/2005 | Antoniou et al. |
| 6,964,951 | B2 | 11/2005 | Antoniou et al. |
| 7,442,787 | B2 | 10/2008 | Antoniou et al. |
| 2003/0166890 | A1 | 9/2003 | Crombie et al. |
| 2004/0148647 | A1 | 7/2004 | Enenkel et al. |

FOREIGN PATENT DOCUMENTS

| | | |
|---|---|---|
| WO | WO94/13273 | 6/1994 |
| WO | WO95/33841 | 12/1995 |
| WO | WO98/07876 | 2/1998 |
| WO | WO 00/05393 | 2/2000 |
| WO | WO 02/24930 | 3/2002 |
| WO | WO 02/081677 | 10/2002 |
| WO | WO 02/099089 | 12/2002 |
| WO | WO 03/006607 | 1/2003 |

OTHER PUBLICATIONS

Lawrence S. Kirschner et al., "Structure Of The Human Ubiquitin Fusion Gene Uba80 (RPS27a) And One Of Its Pseudogenes," *Unit on Genetics and Endocrinology, Developmental Endocrinology Branch, National Institute of Child Health and Human Development, National Institutes of Health*, Bethesda, Maryland 20892, Biochemical and Biophysical Research Communications 270, pp. 1106-1110 (2000), 0006-291X/00, http://www.idealibrary.com.

Daniel Finley et al., "The Tails Of Ubiquitin Precursors Are Ribosomal Proteins Whose Fusion To Ubiquitin Facilitates Ribosome Biogenesis," *Department of Biology, Massachusetts Institute of Technology*, Cambridge, Massachusetts 02139, Nature vol. 338, Mar. 30, 1989, pp. 394-401.

Yuen-Ling Chan et al., "The Carboxyl Extensions Of Two Rat Ubiquitin Fusion Proteins Are Ribosomal Proteins S27a And L40," *Department of Biochemistry and Molecular Biology, The University of Chicago*, Chicago, Illinois 60637, Biochemical And Biophysical Research Communications, vol. 215, No. 2, Oct. 13, 1995, pp. 682-690, 0006-291X/95.

Narayanan Hariharan et al., "Euipotent Mouse Ribosomal Protein Promoters Have A Similar Architecture That Includes Internal Sequence Elements," *Institute for Cancer Research, Fox Chase Cancer Center*, Philadelphia, Pennsylvania 1911, Genes & Development 3: 1789-1800, 1989, ISSN 0890-9369/89.

Olivier Coux, et al., "Structure And Functions Of The 20S and 26S Proteasomes," Annu. Rev. Biochem. 1996, 65:801-847, 1996.

Kent L. Redman et al., "The cDNA For The Ubiquitin-52-Amino-Acid Fusion Protein From Rat Encodes A Previously Unidentified 60 S Ribosomal Subunit Protein," Biochem J. (1996) 315, pp. 315-321 (Printed in Great Britain).

Robert P. Perry, "The Architecture Of Mammalian Ribosomal Protein Promoters,"BioMed Central, BMC Evolutionary Biology, 2005, 5:15, http://www.biomedcentral.com/1471-2148/5/15.

Peter Gunning et al., A human B-actin expression vector system directs high-level accumulation of antisense transcripts, Proc. Natl. Acad. Sci, vol. 84, pp. 4831-4835, Jul. 1987.

M. Garidiner-Garden et al., CpG Islands in Vertebrate Genomes, J. Mol. Biol. 196, 261-282, 1987.

Bonifer, "Long-distance chromatin mechanisms controlling tissue-specific gene locus activation", Gene, 238(2):277-289, Oct. 1999.

Anderson, "Human gene therapy", Nature, 392(Supp):25-30, Apr. 1998.

Verma et al., "Gene therapy-promises, problems and prospects", Nature, 389:239-242, Sep. 1997.

(Continued)

*Primary Examiner*—James Martinell

(57) ABSTRACT

The invention relates to genetic elements capable of improving the levels of expression of operably-linked transcription units. In particular, said genetic elements are derived from the 5' untranslated regions of ribosomal protein genes and may comprise a CpG island. Also provided are vectors and host cells comprising said genetic elements and methods of use to obtain high levels of recombinant gene expression.

27 Claims, 6 Drawing Sheets

OTHER PUBLICATIONS

Corcoran et al., "High-level regulated expression of the human G6PD gene in transgenic mice", Gene, 173(2):241-246, Sep. 1996.
Biamonti et al., "Two homologous genes, originated by duplication, encode the human hnRNP proteins A2 and A1", Nucl. Acids Res., 22(11):1996-2002, Jun. 1994.
Genbank Accession No., U09120, National Library of Medicine, accessed by PTO, Jul. 5, 2000, Dec. 1994.
Genbank Accession No. D28877, National Library of Medicine, accessed by PTO, Jul. 5, 2000, Feb. 1999.
Genbank Accession No. AL031259, version AL031259.7 Gi:3676176, accessed by PTO, Jul. 13, 2000, Sep. 1998.
Chalut et al., "Genomic structure of the human TATA-box-binding protein (TBP)", Gene, 161 (2):277-282, Aug. 1995.
Foulds et al., "Analysis of the human TATA binding protein promoter and identification of an Ets site orifice for activity", Nucl. Acids Res., 25(12):2485-2494, Jun. 1997.
Li et al, "Locus control regions: coming of age at a decade plus", Trends in Genetics, 15 (10):403-408, Oct. 1999.
Chung et. al.; Characterization of the chicken β-globin insulator, 1997, Proc..Natl. Acad. Sci. vol. 94: 575-580.
Crane-Robinson, C. et al., "Chromosomal mapping of core histone acetylation by immunoselection," Methods, 1997, 12(1), 48-56 (summary only).
DiBartolomeis, S.M. et al., "A superfamily of Drosophila satellite related (SR) DNA repeats restricted to the X chromosome euchromatin," Nucl. Acids Res., 1992, 20(5), 1113-1116.
Duhig, T. et al., "The Human Surfeit Locus," Genomics, 1998, 52, 72-78.
Ellis, J. et al., "A dominant chromatin-opening activity in 5' hypersensitive site 3 of the human β-globin locus control region,".EMBO J., 1996, 15(3), 562-568.
Ellis, J. et al., "Evaluation of β-globin gene therapy constructs in single copy transgenic mice," Nucl. Acids Res., 1997, 26(6), 1296-1302.
Gaston, K. et al., "CpG methylation has differential effects on the binding of YY1 and Ets proteins to the bi-directional promoter of the Surf-1 and Surf-2 genes," Nucl. Acids Res., 1995, 23(6), 901-909.
Gaston, K. et al., "YY1 is involved in the regulation of the bi-directional promotor of the Surf-1 and Surf-2 genes," FEBS Letts., 1994, 347, 289-294.
Garson, K. et al., "Surf5: A Gene in the Tightly Clustered Mouse Surfeit Locus is Highly Conserved and Transcribed Divergently from the rpL7a (Surf 3) Gene," Genomics, 1996, 30, 163-170.
Gayalas, A. et al., "Analysis of the chicken GPAT/AIRC bidirectional promoter for de novo purine nucleotide synthesis," J. Biol. Chem., 1995, 270(5), 2403-2410.
Lavia, P. et al., "Coincident start sites for divergent transcripts at a randomly selected CpG-rich island of mouse," EMBO J., 1987, 6, 2773-2779.
Ortiz. S.D. et al., "Adjacent DNA elements dominantly restrict the ubiquitous activity of a novel chromatin-opening region to specific tissues," EMBO J., 1997, 16, 5037-5045.
Palmiter, "The elusive function of metallothioneins," Proc. Natl. Acad. Sci. USA, 1998, 95, 8428-8430.
Talbot, D. et al., "The 5' flanking region of the rat LAP (C/EBPβ) gene can direct high-level position-independent, copy number-dependent expression in multiple tissues in transgenic mice," Nucl. Acids Res., 1994, 22(5), 756-766.
Williams, T.J. et al., "The MES-1 Murine Enhancer Element is Closely Associated with the Heterogeneous 5' Ends of Two Divergent Transcription Units," Mol. Cell. Biol., 1986, 6(12), 4558-4569.
Winston, J. H. et al., "An intron 1 regulatory region from the murine adenosine deaminase gene can activate heterologous promoters for ubiquitous expression in transgenic mice," Som. Cell Mol. Genet., 1996, 22, 261-278.
Festenstein, R., et al., "Locus control region function and heterochromatic-induced position effect variegation," Science, 1996, 271(23), 1123-1125.
Gavalas, a., et al., "Coexpression of two closely linked avian genes for purine nucleotide synthesis from a bidirectional promoter," Mol. Cell Biol., 1983, 13(8), 4784-4792.

Huxley, C., et al., "The mouse surfeit locus contains a cluster of six genes associated with four Gp G-rich islands in 32 kilobases of genomic DNA," Mol. Cell Biol., 1990, 10(2), 605-614.
Ohbayashi, T., et al., "Promoter structure of the mouse TATA-binding protein (TBP) gene," Biochem. Biophys. Res. Commun., 1996, 225(1), 275-280.
Ryan M.T., et al., "The genes encoding mammalian chaperonin 60 and chaperonin 10. are linked head-to-head and share a bidirectional promoter," Gene: an International J on Genes and Genomes, 1997, 196(1-2), 9-17.
Ursini, et al., 1990, High levels of transcription driven by a 400 bp segment of the human G6PD promotor, Biochem Biophys. Res. Commun., 170:1203-1209.
Shewchuk and Hardison, "CpG Islands from the o-Globin Gene Cluster Increase Gene Expression in an Integration-Dependend Manner," Molecular and Cellular Biology. Oct., 1997, 17(10):5856-5866.
Larsen, F. et al., "CpG Islands as Gene Markers in the Human Genome," Genomics, 1992, 13:1095-1107.
Pikaart, Michael'J., "Loss of transcriptional activity of a transgene is accompanied by DNA methylation and histone deacetylation and is prevented by insulators," Genes and Development, 1998, 12:2852-2862.
Recillas-Targa, F. et al., "Positional enhancer-blocking activity of the chicken β-globin insulator in tranciently transfected cells," Proc. Natl. Acad. Sci. USA, 1999, 96(25):14354-14359.
Ng et al., "Evolution of the Functional Human β-Actin Gene and Its MultiPseudogene Family: Conservation of Noncoding Regions and Chromosomal Dispersion of Pseudogenes," Mol. Cell. Biol., vol. 5, 1985, pp. 2720-2732.
Antequera, F. & Bird, A., "Number of CpG islands and genes in human and mouse" Proc. Natl. Acad. Sci. USA, 1993, 90, 11995-11999. .
Bell, A.C. & Felsenfield, G., "Stopped at the border: boundaries and insulators" Curr. Opin. Genet. Dev.,1999, 9, 191-198.
Bird et al., A fraction of the mouse genome that is derived from islands of nonmethylated, CpG-rich DNA, Cell, 1985, 40:91-99.
Dillon, N. & Grosveld, F., "Chromatin domains as potential units of eukaryotic gene function" Curr. Opin. Genet. Dev., 1994, 4, 260-264.
Hammer, et al., "Production of transgenic rabbits, sheep and pigs by microinjection" Nature, 1985, 315:680-683.
Hicks, et al., "Functional genomics in mice by tagged sequence mutagenesis" Nature Genetics, 1997, 16, 338-344.
Kioussis, D. & Festenstein, R., "Locus control regions: overcoming heterochromatin-induced gene inactivation in mammals" Curr. Opin. Genet. Dev.,1997, 7, 614-619.
Needham, et al., "Further development of the locus control region/ murine erthroleukemia expression system: high level expression and characterization of recombinant human calcitonin receptor" Protein Expr. Purif., 1995, 6:124-131.
Sabbattini, P., Georgiou, A., Sinclaire, C. & Dillon, N., "Analysis of mice with single and multiple copies of transgenes reveals a novel arrangement for the Jambda.5-V-preBI locus control region" Mol. Cell. Biol, 1999,19, 671-679.
Tazi, J. & Bird, A., "Alternative chromatin structure at CpG islands",Cell 60,1990, 909-920.
Cavazzana-Calvo, M., et al., "Gene Therapy of Human Severe Combined Immunodeficiency (SCID)-X1 Disease," Science, 288:669-672, (2000).
Cheng, L., et al., "A GFP reporter system to assess gene transfer and expression in human hematopoietic progenitor cells," Gene Therapy, 4:1013-1022, (1997).
Cheng, L., et al., "Sustained Gene Expression in Retrovirally Transduced, Engrafting Human Hematopoietic Stem Cells and Their Lympho-Myeloid Progeny," Blood, 92(1):83-92, (Jul. 1, 1998).
Elwood, N. J., et al., "Retroviral Transduction of Human Progenitor Cells: Use of Granulocye Colony-Stimulating Factor Plus Stem Cell Factor to Mobilize Progenitor Cells In Vivo and Stimulation by Flt3/Flk-2 Ligand in Vitro," Blood, 88(12):4452-4462, (Dec. 15, 1996).
Lu, L., et al., "High Efficiency Retroviral Mediated Gene Trnasduction into Single Isolated Immature and Replatable CD34.sup.3+ Hematopoietic Stem/Progenitor Cells from Human Umbilical Cord Blood ," J. Exp. Med., 178:2089-2096, (Dec., 1993).

Whitwam, T., et al., "Retroviral Marking of Canine Bone Marrow: Long-Term, High-Level Expression of Human Interleukin-2 Receptor Common Gamma Chain in Canine Lymphocytes," Blood, 92(5):1565-1575, (Sep. 1, 1998).

Webpage, the National Institutes for Health for Severe Combined Immunodeficiency ("SCID") in 1990.

Hardison, R., "Hemoglobins from Bacteria to Man: Evolution of Different Patterns of Gene Expression," J. of Experimental Biology 201, 1099-1117 (Mar. 1998), Cambridge, UK.

Juengst, "What next for human gene therapy," Brit. Med. J., vol. 326, pp. 1410-1411.

Williams Steve et al., "CpG-island fragments from the HNRPA2B1/CBX3 genoic locus reduce silencing and enhance transgene expression from the hCMV promoter/enhancer in mammalian cells" BMC Biotechnology, Biomed Central Ltd, London GB, 5(1) pg. 17, Jun. 3, 2005.

Ponger Loic et al., "CPGProD: Identifying CpG islands associated with transcription start sites in large genomic mammalian sequences", Bioinformatics (Oxford) 18(4), pg. 631-633, Apr. 2002.

Database EMBL (online), "Mus musculus ribosomal protein S3 (Rps3) gene, complete cds; and U15a snoRNA and U15b snoRNA genes, complete sequence." EPI assession no. EM: AY0432961 Database assession no. AY043296.

Database EMBL (online), "H015123S Ho Hordeum vulgare cDNA clone H015123 5-Prime, mRNA sequence." EBI acession no. EM_PRO:CD057580. Database accession no. CD057580.

Kozu, T. et al., Structure and Expression of the Gene (HNRPA2B1) Encoding the Human HNRNP Protein A1/B1: Genomics, Academic Press, 25(2), pp. 365-371, Jan. 20, 1995.

Antoniou, M. et al., "Transgenes encompassing dual-promote CpG islands from the human TBP and HNRPA2B1 loci are resistant to heterochromatin-mediated silencing." Genomics, Academic Press, 82(3), pp. 269-279, Sep. 3, 2002.

International Search Report, WO 2006/123097, Oct. 30, 2006, ISA/EP.

A

B

A

B

US 7,632,661 B2

EXPRESSION ELEMENTS

CROSS-REFERENCE TO RELATED APPLICATIONS

This application claims priority from GB Application # GB 0509965.0, filed May 17, 2005 and U.S. Provisional Patent Application No. 60/682,277, filed May 18, 2005, the contents which are hereby incorporated by reference in full.

BACKGROUND

The present invention relates to polynucleotides comprising elements conferring improved expression on operably-linked transcription units. These elements are naturally associated with the promoter regions of ribosomal protein genes and, in recombinant DNA constructs, confer high and reproducible levels of gene expression. The present invention also relates to vectors comprising such polynucleotide sequences, host cells comprising such vectors and use of such polynucleotides, vectors or host cells in therapy, for production of recombinant proteins in cell culture and other biotechnological applications.

The current model of chromatin structure in higher eukaryotes postulates that genes are organised in "domains" (Dillon, N. & Grosveld, F. Chromatin domains as potential units of eukaryotic gene function. *Curr. Opin. Genet. Dev.* 4, 260-264 (1994); Higgs, D. R. Do LCRs open chromatin domains? *Cell* 95, 299-302 (1998)) Chromatin domains are envisaged to exist in either a condensed, "closed", transcriptionally silent state, or in a de-condensed, "open" and transcriptionally competent configuration. The establishment of an open chromatin structure characterised by increased DNaseI sensitivity, DNA hypomethylation and histone hyperacetylation, is considered a pre-requisite to the commencement of gene expression.

The open and closed nature of chromatin regions is reflected in the behaviour of transgenes that are randomly integrated into the host cell genome. Identical constructs give different patterns of tissue-specific and development stage-specific expression when integrated at different locations in the mouse genome (Palmiter, R. D. & Brinster, R. L. *Ann. Ref. Genet.* 20, 465-499 (1986); Allen, N. D. et al. *Nature* 333, 852-855 (1988); Bonnerbt, C., Grimber, G., Briand, P. & Nicolas, J. F. *Proc. Natl. Acad. Sci. USA* 87:6331-6335 (1990)).

The chromatin domain model of gene organisation suggests that genetic control elements that are able to establish and maintain a transcriptionally competent open chromatin structure should be associated with active regions of the genome.

Locus Control Regions (LCRs) are a class of transcriptional regulatory elements with long-range chromatin remodelling capability. LCRs are functionally defined in transgenic mice by their ability to confer site-of-integration independent, transgene copy number-dependent, physiological levels of expression on a gene linked in cis, especially single copy transgenes Fraser, P. & Grosveld, F. *Curr. Opin. Cell Biol.* 10, 361-365 (1998); Li, Q., Harju, S. & Peterson, K. R. *Trends Genet.* 15: 403-408 (1999). Crucially, such expression is tissue-specific. LCRs are able to obstruct the spread of heterochromatin, prevent PEV (Kioussis, D. & Festenstein, R. *Curr. Opin. Genet. Dev.* 7, 614-619 (1997)) and consist of a series of DNase I hypersensitive (HS) sites which can be located either 5' or 3' of the genes that they regulate (Li, Q., Harju, S. & Peterson, K. R. *Trends Genet.* 15:403-408 (1999)).

The generation of cultured mammalian cell lines producing high levels of a therapeutic protein product is a major developing industry. Chromatin position effects make it a difficult, time consuming and expensive process. The most commonly used approach to the production of such mammalian "cell factories" relies on gene amplification induced by a combination of a drug resistance gene (e.g., DHFR, glutamine synthetase (Kaufman R J. *Methods Enzymol* 185, 537-566 (1990)). and the maintenance of stringent selective pressure. The use of vectors containing LCRs from highly expressed gene domains, using cells derived from the appropriate tissue, greatly simplifies the procedure, giving a large proportion of clonal cell lines showing stable high levels of expression (Needham M, Gooding C, Hudson K, Antoniou M, Grosveld F and Hollis M. *Nucleic Acids Res* 20, 997-1003 (1992); Needham M, Egerton M, Millest A, Evans S, Popplewell M, Cerillo G, McPheat J, Monk A, Jack A, Johnstone D and Hollis M. *Protein Expr Purif* 6,124-131 (1995).

However, the tissue-specificity of LCRs, although useful in some circumstances, is also a major limitation for many applications, for instance where no LCR is known for the tissue in which expression is required, or where expression in many, or all, tissues is required.

U.S. Pat. No. 6,689,606 and co-pending patent application WO 00/0539, incorporated by reference herein, describe elements that are responsible, in their natural chromosomal context, for establishing an open chromatin structure across a locus that consists exclusively of ubiquitously expressed, housekeeping genes. These elements are not derived from an LCR and comprise extended methylation-free CpG islands.

In mammalian DNA, the dinucleotide CpG is recognised by a DNA methyltransferase enzyme that methylates cytosine to 5-methylcytosine. However, 5-methylcytosine is unstable and is converted to thymine. As a result, CpG dinucleotides occur far less frequently than one would expect by chance. Some sections of genomic DNA nevertheless do have a frequency of CpG that is closer to that expected, and these sequences are known as "CpG islands". As used herein a "CpG island" is defined as a sequence of DNA, of at least 200 bp, that has a GC content of at least 50% and an observed/expected CpG content ratio of at least 0.6 (i.e. a CpG dinucleotide content of at least 60% of that which would be expected by chance) (Gardiner-Green M and Frommer M. *J Mol Biol* 196, 261-282 (1987); Rice P, Longden I and Bleasby A *Trends Genet* 16, 276-277 (2000).

Methylation-free CpG islands are well-known in the art (Bird et al (1985) *Cell* 40: 91-99, Tazi and Bird (1990) *Cell* 60: 909-920) and may be defined as CpG islands where a substantial proportion of the cytosine residues are not methylated and which usually extend over the 5' ends of two closely spaced (0.1-3 kb) divergently transcribed genes. These regions of DNA are reported to remain hypomethylated in all tissues throughout development (Wise and Pravtcheva (1999) *Genomics* 60: 258-271). They are often associated with the 5' ends of ubiquitously expressed genes, as well as an estimated 40% of genes showing a tissue-restricted expression profile (Antequera, F. & Bird, A. *Proc. Natl. Acad. Sci. USA* 90, 1195-11999 (1993); Cross, S. H. & Bird, A. P. *Curr. Opin, Genet. Dev.* 5, 309-314 (1995) and are known to be localised regions of active chromatin (Tazi, J. & Bird, A. *Cell* 60, 909-920 (1990).

An 'extended' methylation-free CpG island is a methylation-free CpG island that extends across a region encompassing more than one transcriptional start site and/or extends for more than 300 bp and preferably more than 500 bp. The borders of the extended methylation-free CpG island are functionally defined through the use of PCR over the region in combination with restriction endonuclease enzymes whose ability to digest (cut) DNA at their recognition sequence is sensitive to the methylation status of any CpG residues that are present. One such enzyme is HpaII, which recognises and digests at the site CCGG, which is commonly found within CpG islands, but only if the central CG residues are not methylated. Therefore, PCR conducted with HpaII-digested DNA and over a region harbouring HpaII sites, does not give an amplification product due to HpaII digestion if the DNA is unmethylated. The PCR will only give an amplified product if the DNA is methylated. Therefore, beyond the methylation-free region HpaII will not digest the DNA a PCR amplified product will be observed thereby defining the boundaries of the "extended methylation-free CpG island".

It has been shown (WO 00/05393) that regions spanning methylation-free CpG islands encompassing dual, divergently transcribed promoters from the human TATA binding protein (TBP)/proteosome component-B1 (PSMB1) and heterogeneous nuclear ribonucleoprotein A2/B1 (hnRNPA2)/heterochromatin protein 1 Hsγ (HP1$^{Hs\gamma}$) gene loci give reproducible, physiological levels of gene expression and that they are able to prevent a variegated expression pattern and silencing that normally occurs with transgene integration within centromeric heterochromatin.

It is known that methylation-free CpG islands associated with actively transcribing promoters possess the ability to remodel chromatin and are thus thought to be a prime determinant in establishing and maintaining an open domain at housekeeping gene loci (WO 00/05393) and that such elements confer an increased proportion of productive gene delivery events with improvements in the level and stability of transgene expression.

Ribosomes are large RNA and protein complexes responsible for the translation of mRNA into polypeptides. Each ribosome is comprised of 4 ribosomal RNA (rRNA) molecules and large number of ribosomal proteins (currently thought to be 79 in mammalian cells). Ribosomal proteins have functions including facilitation of rRNA folding, protection from cellular ribonucleases, and coordinating protein synthesis. Some ribosomal proteins have additional extraribosomal functions (Wool, 1996, TIBS 21: 164-165). Given the structural and functional similarities of ribosomes across species, it is unsurprising that the amino acid sequence conservation of ribosomal proteins is high, and among mammals the sequences of most ribosomal proteins are almost identical (Wool et al, 1995, Biochem Cell Biol 73: 933-947).

Two ribosomal proteins appear atypical in that they are expressed in the form of propeptides (carboxy-extension proteins) fused to ubiquitin. Ubiquitin is a highly conserved 76-residue polypeptide involved in a variety of cellular functions, including the regulation of intracellular protein breakdown, cell cycle regulation and stress response (Hershko & Ciechanover, 1992, Annu Rev Biochem 61: 761-807; Coux et al, 1996, Annu Rev Biochem 65: 801-847).

Ubiquitin is encoded by two distinct classes of gene. One is a poly-ubiquitin gene encoding a linear polymer of ubiquitin repeats. The other comprises genes encoding natural fusion proteins in which a single ubiquitin molecule is linked to the ribosomal protein rps27A or rpL40 (Finley et al, 1989, Nature 338: 394-401; Chan et al, 1995, Biochem Biophys Res Commun 215: 682-690; Redman & Burris, 1996, Biochem J 315: 315-321).

The common structural features of ribosomal protein promoters are discussed by Perry (2005, BMC Evolutionary Biology 5:15). The promoters may be classified according to the nature of the TATA box motifs, number and type of transcription factor binding sites and location of AUG start codons. However, such classification does not appear to predict promoter strength and evidence suggests that several such promoters tested have equivalent transcriptional activity as measured by expression of a linked reporter gene (Hariharan et al, 1989, Genes Dev 3: 1789-800).

U.S. Pat. No. 6,063,598 discloses the hamster-ubiquitin/S27a promoter its use to drive high level production of recombinant proteins. However, there is no suggestion of its use to enhance the expression of a gene primarily transcribed from a further promoter (i.e one other than hamster-ubiquitin/S27a promoter).

US application US 2004/0148647 discloses a reporter assay using an expression vector comprising a hamster ubiquitin /S27A promoter functionally linked to a gene for a product of interest and a fluorescent protein reporter. Again, the application only discloses constructs in which transcription of gene of interest is from the hamster-ubiquitin/ S27a promoter itself.

It remains an objective in the field of recombinant gene expression to obtain higher and more reliable levels of expression, particularly for in vivo and ex vivo therapeutic applications and for in vitro recombinant protein production.

SUMMARY OF THE DISCLOSURE

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

As used herein, a promoter region is defined as being a genomic nucleotide sequence consisting of a promoter and transcriptional start site together with 5 kb of 5' sequence upstream of the transcriptional start site and 500 bp 3' sequence downstream of the distal end of the first exon.

A 5' untranslated region means a region 5' of the translational start encoded in the genomic or cDNA sequence. It is taken to include all upstream regulatory elements. A 5' upstream sequence is used to mean sequence 5' to the transcriptional start encoded in the genomic sequence.

As used herein, 'transcribable nucleic acid' means a nucleic acid which, when operably linked to a functional promoter and other regulatory sequences, is capable of being transcribed to give a functional RNA molecule, such as mRNA. Such sequences may comprise open reading frames, which encode translatable polypeptide sequences. Alternatively, the functional RNA may have another function, such as ribosomal RNA, ribozymes or antisense RNA.

'Gene' is commonly taken to means the combination of the coding region of the transcribable nucleic acid, together with the promoter from which it is transcribed and other regulatory sequences such as enhancers and 3' polyadenylation signals. In genomic DNA genes also contain introns. 'Transcription unit' is sometimes used to describe a functional combination of at least a promoter and minimal regulatory sequences with a transcribable nucleic acid, often derived from cDNA from which the introns have been spliced out. 'Cistron' is defined as a nucleic acid encoding a single polypeptide together with functional initiation and termination signals. 'Transgene' implies a gene that has been transferred from one genome to another, although the term may be more loosely applied to any gene or even transcribable nucleic acid comprised in a recombinant DNA construct such as a vector.

Promoter and enhancer are terms well known in the art and include the following features which are provided by example only, and not by way of limitation. Promoters are 5', cis-acting regulatory sequences directly linked to the initiation of transcription. Promoter elements include so-called TATA box and RNA polymerase initiation selection (RIS) sequences which function to select a site of transcription initiation. These sequences also bind polypeptides which function, inter alia, to facilitate transcription initiation selection by RNA polymerase.

In simple terms, promoters are directional elements that act to initiate transcription of sequences situated less than 100 (and usually less than 50) nucleotide base pairs (bp) downstream. They contain a number of short consensus nucleotide sequences that act as binding sites for various proteins that participate in the initiation of transcription and the assembly of a multi-subunit complex known as the pre-initiation complex (McKnight and Tjian, 1987, Cell 46: 795-805). In most genes, this occurs at a very widely conserved sequence known as the TATA box (TATAAA) to which the TATA box-binding protein (TBP, a subunit of the general transcription factor TFIID) binds. There follows an ordered assembly of more than ten further transcription factors to finally form the Pol II holoenzyme complex. RNA transcription actually starts at an initiator site about 25-30 bases downstream (Breathnach and Chambon, 1981, Annu Rev Biochem 50: 349-393) to which TBP also binds.

Most functional promoters contain further upstream promoter elements (UPEs), of which the most highly conserved are the CAAT box (CCMT, the binding site for the transcription factors CBF, C/EBP and NF-1), about 70-200 bp upstream, and the GC box (GGGCGG, binding site for the general transcription factor Sp-1) a similar distance upstream. Although basal levels of transcription occur from the TATA box alone, for most promoters at least the CAAT and GC boxes are required for optimal levels of transcription.

Enhancers are sequences that act non-directionally to increase transcription from promoters situated locally but not necessarily immediately adjacent (up to several kilobases away (Kadonaga (2004) Cell 116: 247-257). Enhancers contain short (8-12 bp) consensus sequences representing the binding sites for a wide range of transcriptional activator proteins (Ondek et al, 1988, Science 236: 1237-1244) including some, such as NF-1 and SP-1 that are also associated with promoter elements. These sequences are often duplicated in tandem or inverted repeats.

In some natural transcription units, including the very active immediate/early gene transcription units of many DNA viruses such as cytomegalovirus, enhancer and promoter elements may be functionally combined into what is effectively one extended upstream element.

Promoters may be regulated, being responsive to cell type, temperature, metal ions or other factors; or constitutive, giving transcription that is unresponsive to such factors. For many purposes a strong, constitutive promoter giving consistent, high levels of transcription in many, if not all, cell types is highly advantageous. For many years the enhancer/promoter element driving immediate/early gene expression in human cytomegalovirus has been very widely used for driving such expression of heterologous genes in eukaryotic expression vectors (Foecking & Hoffstetter, 1986, Gene 45: 101-105).

It was hypothesised that promoter regions of ribosomal protein genes might have useful activity in boosting and stabilising expression of linked transgenes and that the regulatory regions from highly expressed genes might be more likely to contain elements that are very effective at maintaining chromatin in a transcriptionally active conformation. The linking of such elements to a heterologous promoter might then generate a more open chromatin environment surrounding that promoter, resulting in increased expression. It will be understood by one of skill in the art that promoters derived from ribosomal protein genes are to be distinguished from ribosomal promoters, which are RNA polymerase Type I dependent promoters from which rRNA is transcribed.

To test the hypothesis, RNA was obtained from exponentially growing CHO-K1 and NSO cell lines and a microarray analysis against 13,443 murine genes was performed. We limited our analysis to elements having a high CpG island content and a likelihood of bi-directional promoters. Using criteria based on the minimal effective sequence from the hnRNPA2 regulatory region, approximately 3 kb of DNA from a selection of these genes was amplified by PCR from NSO genomic DNA. These sequences were then cloned into EGFP expression vectors and transfected into CHO-K1 along with hnRNPA2 control versions of the same vector.

It was found that sequences derived from the promoter regions of two ribosomal proteins gave consistently high levels of expression of the heterologous reporter sequence in the assay used. In each case, the promoter region comprised a GC-rich sequence extending from the 5' region upstream of the actual promoter elements well into the first exon and, indeed into the first intron. This GC-rich sequence fulfilled the criteria of being an extended CpG island, as defined herein as extending over 300 bp.

Accordingly, the invention provides an isolated polynucleotide comprising a) an element comprising at least 500 contiguous nucleotides from the promoter region of a ribosomal protein gene b) a heterologous promoter c) a transcribable nucleic acid sequence adjacent said heterologous promoter wherein the transcribable nucleic acid sequence is transcribed from said heterologous promoter and the level of said transcription is enhanced by said element. an element. Preferably said element comprises more than 1 kb and most preferably more than 3 kb 5' untranslated sequence from a ribosomal protein gene.

The contiguous nucleotides are selected from the promoter area, which extends from a point 5 kb upstream (5' relative to the sense strand) of the transcriptional start site to a point 500 bp downstream (3' relative to the sense strand) of the distal (3') end of the first exon.

Preferably said ribosomal protein gene is selected from the list consisting of RPSA, RPS2, RPS3, RPS3A, RPS4, RPS5, RPS6, RPS7, RPS8, RPS9, RPS10, RPS11, RPS12, RPS13, RPS14, RPS15, RPS15A, RPS16, RPS17, RPS18, RPS19, RPS20, RPS21, RPS23, RPS24, RPS25, RPS26, RPS27, RPS27A, RPS28, RPS29, RPS30, RPL3, RPL4, RPL5, RPL6, RPL7, RPL7A, RPL8, RPL9, RPL10, RPL10A, RPL11, RPL12, RPL13, RPL13A, RPL14, RPL15, RPL17, RPL18, RPL18A, RPL19, RPL21, RPL22, RPL23, RPL23A, RPL24, RPL26, RPL27, RPL28, RPL29, RPL30, RPL31, RPL32, RPL34, RPL35, RPL35A, RPL36, RPL36A, RPL37, RPL37A, RPL38, RPL39, RPL41, RPLPO, RPLP1 and RPLP2 and their orthologues. More preferably it is RPS3 or RPS11.

In one preferred embodiment the element comprises a CpG island, preferably an extended CpG island of at least 300 bp and more preferably 500 bp. Preferably the CpG island is unmethylated. It is also preferred that said element comprises the promoter from a ribosomal protein gene and from which transcription of the ribosomal protein gene is naturally initiated. Such a promoter is often referred to as the endogenous promoter. In a preferred embodiment, the element further comprises or more exons of said ribosomal protein gene.

It is preferred that the ribosomal protein gene is a mammalian gene, although such genes and their promoters and 5' upstream sequences are highly conserved across species and might alternatively be an insect, nematode or yeast gene. Preferably, however, it is a human or rodent gene and most preferably it is a mouse gene.

In a highly preferred embodiment, the isolated polynucleotide of the invention comprises nucleotides 38 to 3154 of the mouse rps3 nucleotide sequence depicted in SEQ ID NO:1. Alternatively it comprises nucleotides 12 to 3032 of the mouse rps 11 nucleotide sequence as listed in SEQ ID NO:2.

In one aspect, in addition to the element described, the polynucleotide further comprises a promoter not naturally associated with said element from a ribosomal protein gene. In this embodiment a heterologous promoter (distinct from the endogenous promoter which may or may not be present in the first element) is situated in an adjacent and operably-linked position downstream from the element containing ribosomal protein gene-derived 5' sequence . In this arrangement, expression directed by this heterologous promoter is enhanced by the effect of the ribosomal protein gene element.

In one embodiment, said promoter is a constitutive promoter, more preferably selected from the list consisting of the cytomegalovirus early/immediate promoter, SV40, EF-1□, Rous sarcoma virus (RSV) LTR, or HIV2 LTR or combinations of sequences derived therefrom. More preferably the promoter is a CMV immediate/early promoter. Most preferably it is the mouse or guinea pig CMV immediate/early promoter.

Alternatively, said promoter may be a tissue-specific promoter, which directs expression in a limited range of tissues. Such promoters are well-known in the art and include those from □-globin, the □ and □ immunoglobulin light chains, immunoglobulin heavy chain, desmin, tyrosinase, CD2, IL-3, myosin light chain, human melanoma inhibitory activity gene promoter and keratins. In a particularly preferred embodiment the promoter is a tumour-selective promoter, which directs expression preferentially one or more tumour types. Examples of such promoters include those from carcinoembryonic antigen (CEA), prostate-specific antigen (PSA), cyclooxygenase-2 (COX-2), alpha-fetoprotein (AFP), tyrosinase, and T-cell Factors 1-4 (TCF) -based promoters.

The transcribable nucleic acid may encode any useful polypeptide for in vitro expression and is preferably selected from the list consisting of an antibody, a functional epitope-binding fragment of an antibody, growth factor, cytokine, protein kinase, soluble receptor, membrane-bound receptor, or blood clotting factor. Alternatively, the transcribable nucleic acid may encode a therapeutic gene of use for in vivo or ex vivo gene therapy. Such a therapeutic nucleic acid may act by replacing or supplementing the function of a defective gene causing a disease such as cystic fibrosis, thalassaemia, sickle anaemia, Fanconi's anaemia, haemophilia, severe combined immunodeficiency (SCID), phenylketonuria (PKU), alpha-1 antitrypsin deficiency, Duchenne muscular dystrophy, ornithine transcarbamylase deficiency or osteogenesis imperfecta. Alternatively, it may encode a cytotoxic agent or prodrug-converting enzyme selectively expressed in a target cell, such as a malignant cancer cell, in order to kill it. Such applications, and many others, are well-known to those of skill in the art and the relevance of the current invention in enhancing the expression of therapeutic nucleic acids will be clear to such skilled practitioners.

In another aspect, the invention provides a vector comprising the polynucleotide of invention as disclosed above. Preferably said vector is an expression vector adapted for eukaryotic gene expression.

Typically said adaptation includes, by example and not by way of limitation, the provision of transcription control sequences (promoter sequences) which mediate cell/tissue specific expression. Adaptations also include the provision of selectable markers and autonomous replication sequences which both facilitate the maintenance of said vector in either the eukaryotic cell or prokaryotic host. Vectors which are maintained autonomously are referred to as episomal vectors. Episomal vectors are desirable since they are self-replicating and so persist without the need for integration. Episomal vectors of this type are described in WO98/07876.

Adaptations which facilitate the expression of vector encoded genes include the provision of transcription termination/polyadenylation sequences. This also includes the provision of internal ribosome entry sites (IRES) which function to maximise expression of vector encoded genes arranged in bicistronic or multi-cistronic expression cassettes.

These adaptations are well-known in the art. There is a significant amount of published literature with respect to expression vector construction and recombinant DNA techniques in general. Please see, Sambrook et al (1989) Molecular Cloning: A Laboratory Manual, Cold Spring Harbour Laboratory, Cold Spring Harbour, N.Y. and references therein; Marston, F (1987) DNA Cloning Techniques: A Practical Approach Vol III IRL Press, Oxford UK; DNA Cloning: F M Ausubel et al, Current Protocols in Molecular Biology, John Wiley & Sons, Inc. (1994).

The vector may be an episomal vector or an integrating vector. Preferably, the vector is a plasmid. Alternatively, the vector may be a virus, such as an adenovirus, adeno-associated virus, a herpesvirus, vaccinia virus, lentivirus or other retrovirus.

Alternatively, such a vector may comprise
a) an element comprising at least 500 contiguous nucleotides from the promoter region of a ribosomal protein gene
b) a heterologous promoter
c) a multiple cloning site wherein a transcribable nucleic acid sequence inserted into said multiple cloning site is capable of being transcribed from said heterologous promoter and the level of said transcription is enhanced by said element.

In a further aspect the invention provides a host cell comprising the isolated polynucleotide or vector as herein described. Preferably said host cell is a mammalian cell, more preferably selected from the list consisting of CHO, NSO, BHK, HeLa, HepG2.

Also provided by the invention is a method of expressing a polypeptide comprising inserting expression vector comprising the polynucleotide of the invention into an appropriate host cell as herein described and culturing said host cell in suitable conditions to allow expression. Preferably said polypeptide is a therapeutically useful polypeptide.

In a further aspect the invention provides a pharmaceutical preparation comprising the polynucleotide, vector or host cell as herein described and a pharmaceutically acceptable carrier, excipient, buffer or medium.

DETAILED DESCRIPTION

Materials and Methods

Figure 1:
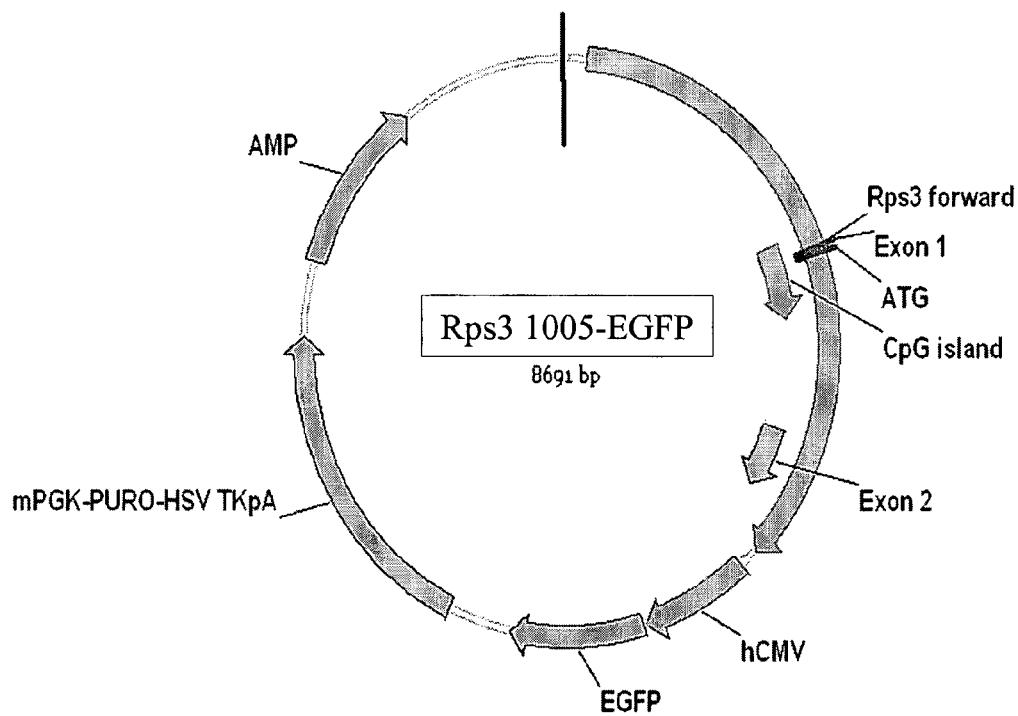
FIG. 1 shows a plasmid map of vector rps3-1005-EGFP (see Example 1).
Figure 2:
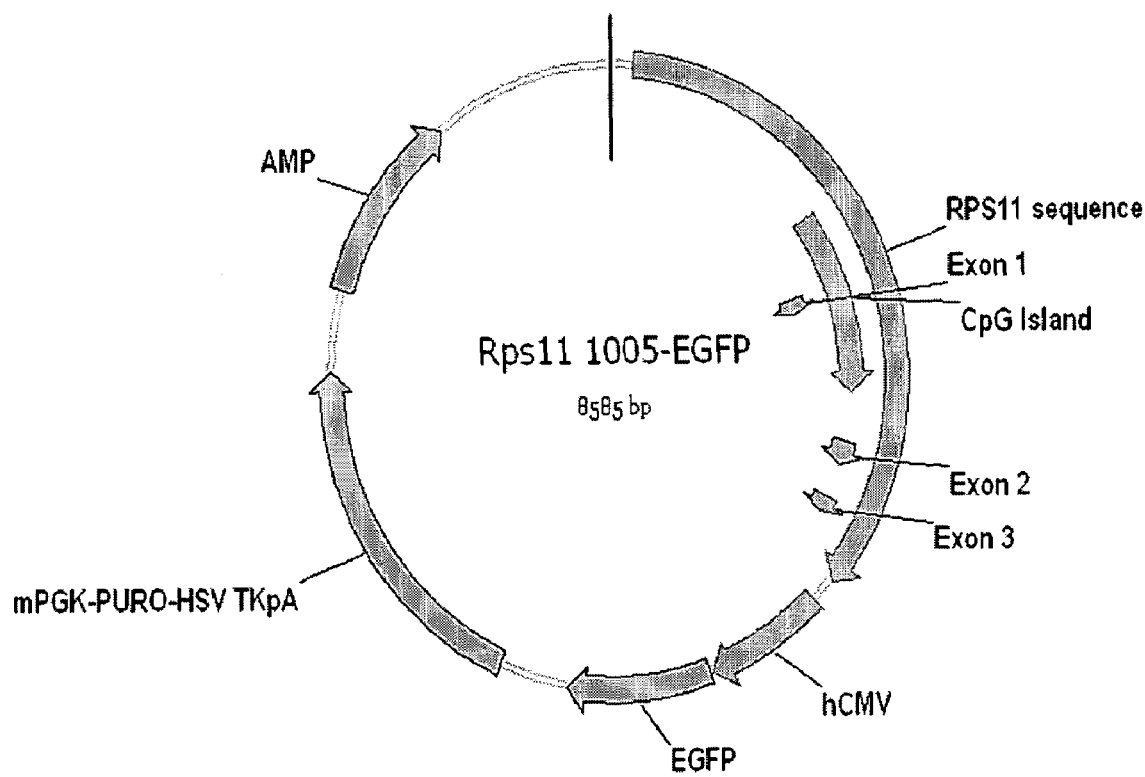
FIG. 2 shows a plasmid map of vector rps11-1005-EGFP (see Example 2).

Microarray Analysis.

Total RNA was extracted from .about.80% confluent CHO-K1 cells using RNeasy RNA extraction kit (Qiagen, Crawley, UK) according to the manufacturers protocol. Total RNA (2 µg/µl) was subjected to microarray expression analysis using the mouse 70-mer oligonucleotide library (Operon V.1) representing 13,443 known transcripts. The University of Cincinnati, Genomics and Microarray Laboratory undertook Microarray analysis according to referenced protocols.

Gene transcript sequences were ranked according to increasing fluorescence. Since our previous study detailed the HNRPA2B1/CBX3 loci as a chromatin-remodelling element and conferring benefit to hCMV the HNRPA2 transcript was identified as the baseline expression level. However, using the available microarray analysis the HNRPA2 transcript was barely detectable. Since the expression level of the HNRPA2 transcript was minimal, using HNRPA2 as our reference would have identified 3829 sequences for potential analysis. Therefore, 7 sequences from the top 2% (76 sequences) of the ordered, expressed transcripts were identified according to the criteria of containing a CpG island and one or more putative/known transcriptional start sites (see Table 1). CpG islands position, size and GC:CG ratios were verified using GrailEXP. Putative/known transcriptional starts sites were identified from NIX blast analysis and Ensembl databases.

PCR Amplification of CpG Island-containing Fragments.

PCR oligonucleotides were designed to amplify approximately 3 kb fragments encompassing the complete CpG island embedded promoter region whilst including approximately 500 bp of coding sequence according to known or predicted coding sequence structure (see Table 2).

PCR reactions contained oligonucleotide sets specific each genomic fragment (2 pmol of each primer; Table 2). PCR amplification was achieved using the Failsafe☐

PCR premixes A-F (Cambio, UK), 1 unit Taq DNA polymerase (Promega, UK) and 200 ng of template DNA. Initial denaturation was 96° C. for 2 min, whilst PCR amplification was carried out for 35 cycles (94° C. for 1 min, 55-60° C. for 1 min, 72° C. for 5 min). A final extension step (72° C. for 10 min) was included.

PCR products were gel purified, using GFX DNA purification columns (Amersham, UK) according to the manufacturers protocol, and subjected to TOPO TA cloning ☐ according to the manufacturers protocol (TOPO; Invitrogen, UK). Sense and anti-sense orientations were obtained for each CpG island-containing fragment cloned into TOPO vectors (Invitrogen, UK).

Expression Vector Construction.

A control expression vector (designated CET1005EGFP, SEQ ID NO:20) was constructed by the insertion of an hCMVIEGFPIsv40 pA (Nhe//Age/ deleted multiple cloning site) from pEGFP-N1 into CET 900 followed by the insertion of the AscI cassette from this vector into the AscI site of CET 1005.

All CpG island fragments were removed from TOPO2.1 (Invitrogen, UK) unless otherwise stated. Terf2ip Acc65I/EcoRV fragment was inserted into Acc65I/SwaI of 1005. GAPDH SpeI/SnaBI was inserted into PmeI/XbaI of 1005. RPS3 XbaI/SpeI fragment was inserted into XbaI of 1005. RPS11 and TUBA1 EcoRI blunt fragments was removed from TOPO4.0 and TOPO2.1 respectively (Invitrogen, UK) and inserted into PmeI of 1005. Finally, A430106P18Rik (EcoRV) and 2510006D16Rik (BstXI) fragments were also inserted into PmeI of 1005. All CpG island containing fragments were inserted in both sense and anti-sense orientations immediately upstream of the hCMV promoter.

Cell Lines and Transfections.

CHO-K1 cells were grown in HAMS F12 (Invitrogen, Paisley, UK) plus 4500 mg/l L-ananyl-L-glutamine, 10 ☐g/ml each of penicillin and streptomycin, and 10% (v/v) heat inactivated foetal calf serum (FCS; Invitrogen, Paisley, UK). Transfection was carried out by electroporation using approximately $10^7$ cells from 80% confluent cultures and a BioRad Gene Pulser II™ set to deliver a single pulse of 975☐F. at 250V. Transfections used 2 ☐g of linearised CET1005EGFP plasmid and equivalent molar quantities for expression vectors of different size. Stably transfected cells were selected and maintained in growth medium containing 12.5 ☐g/ml puromycin sulphate (Sigma, UK).

Quantification of Transgene Expression

Analysis of cells transfected with EGFP reporter constructs was with a Becton-Dickinson FACScan using the parental CHO-K1 cell line as a background, autofluorescence control.

TABLE 1

Sequences analysed

| Locus | Acc. #[a] | Description[b] | bp | CpG island[c] % CG | GC/CG |
|---|---|---|---|---|---|
| Terf2ip | AB041557 | Telomeric repeat binding factor 2 interacting protein 1 (TRF2-interacting telomeric protein Rap1). | 968 | 64.56 | 0.90 |
| Gapd[d] | M32599 | Glyceraldehyde-3-phosphate dehydrogenase | 1187 | 60.50 | 0.84 |
| RPS3 | NM012052 | RPS3 - 40S ribosomal protein S3. | 419 | 60.39 | 0.87 |
| TUBA1 | M13445 | Tubulin alpha-1 chain (Alpha-tubulin 1). | 850 | 66.30 | 0.91 |
| RPS11 | AK011207 | RPS11 - 40S ribosomal protein S11. | 957 | 59.71 | 0.95 |
| A430106P18 Rik | AK020778 | Expressed sequence tag | 982 | 63.62 | 0.93 |
| 2510006D16 Rik | AK010915 | Expressed sequence tag | 679 | 67.69 | 0.75 |

[a]Genbank Accession
[b]Enseml description
[c]Grailexp
[d]Gapd - derived from human sequence

TABLE 2

PCR oligonucleotides and amplicon sizes

| Locus | Sense | Antisense | Amplicon |
|---|---|---|---|
| Terf2ip | gtagtttctgacttggaaatgt (SEQ ID NO: 3) | aactgacctgccatgccattc (SEQ ID NO: 4) | 2995 bp |
| Gapd | gagcagtccggtgtcacta (SEQ ID NO: 5) | gcagagaagcagacagttatg (SEQ ID NO: 6) | 3096 bp |
| RPS3 | cagagcatcaagtacctgtga (SEQ ID NO: 7) | taaccactaagccatctctcc (SEQ ID NO: 8) | 3056 bp |
| TUBA1 | caagaacaaggaagctggcc (SEQ ID NO: 9) | taaaacccacagcactgtaggg (SEQ ID NO: 10) | 3049 bp |
| RPS11 | aagactgtttgcctcatgcc (SEQ ID NO: 11) | ggatgacaatggtcctctgc (SEQ ID NO: 12) | 3020 bp |
| A430106P18Rik | atggttgtaggttcacgtcc (SEQ ID NO: 13) | atccctcacattgccaagcc (SEQ ID NO: 14) | 3128 bp |
| 2510006D16Rik | acttaagacctgatgcctcc (SEQ ID NO: 15) | gctagcttacataggcagcc (SEQ ID NO: 16) | 2997 bp |

EXAMPLE 1 rps3 Element Driven Expression

SEQ ID NO:1 shows the RPS3 cloned sequence (Nucleotides 38 to 3154); SEQ ID NO:17 shows the complete plasmid sequence of pRPS3-1005-EGFP; SEQ ID NO:18 shows the complete plasmid sequence of pCET1015-EGFP.

EGFP expression levels, 8 days post-transfection, were investigated, within CHO-K1 pools containing hCMV alone (control construct; plasmid pCET1005-EGFP, linearised with PmeI prior to transfection), constructs containing an 8 kb RNPA2 fragment (plasmid pCET1015-EGFP, linearised with PmeI prior to transfection) and Rps3 (plasmid pRPS3-1005-EGFP; linearised with PmeI prior to transfection).

Pools generated with Rps3 containing constructs show a significant increase in EGFP expression levels compared to control constructs. Addition of the Rps3 sequence upstream of the hCMV promoter resulted in a 5.5- or 1.5-fold increase in mean fluorescence intensity relative to the control or hnRNPA2 element containing constructs respectively (FIG. 3A).

The activity of the constructs was investigated in NS0 cells. The increase in mean fluorescence intensity in stable pools when RPS3 element or hnRNPA2 elements are included in the constructs, compared to the hCMV promoter alone, was 28-fold or 18-fold respectively (FIG. 5A).

Figure 3:
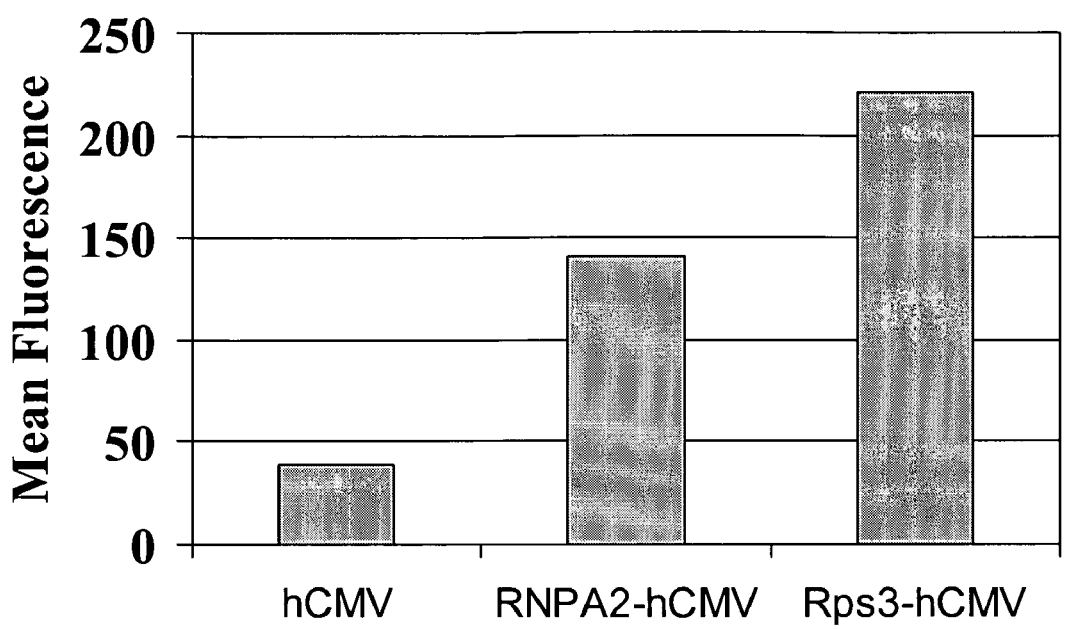
FIG. 3 shows the expression of the EGFP reporter as expressed by various rps3 constructs in CHO-K1 cells analysed by FACS analysis, 8 days post transfection. Figure A shows mean fluorescence, and Figure B a indicates the percentage of cells expressing the reporter gene to a detectable level (% positive cells). See Example 1.
Figure 3:
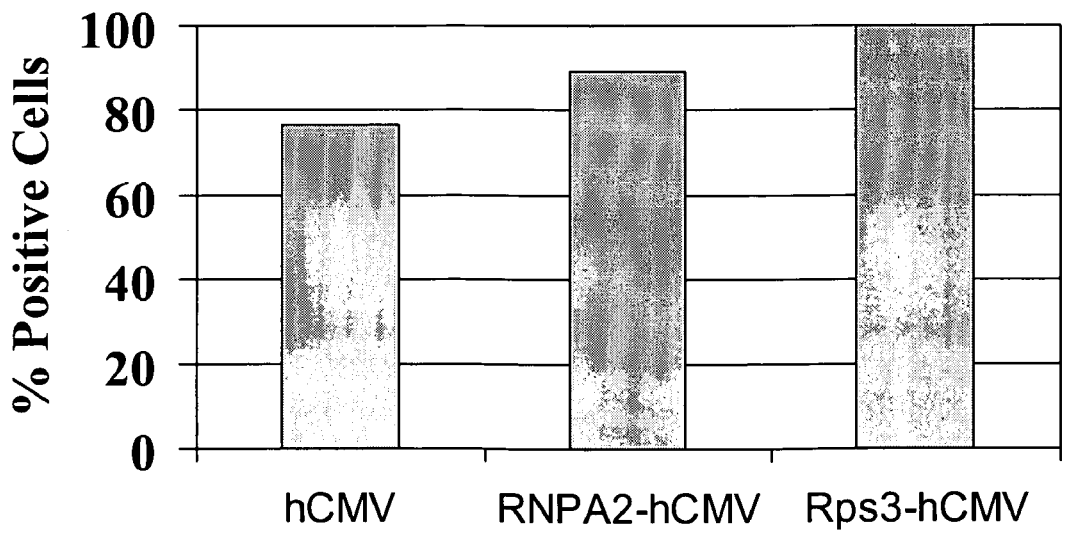
Figure 5:
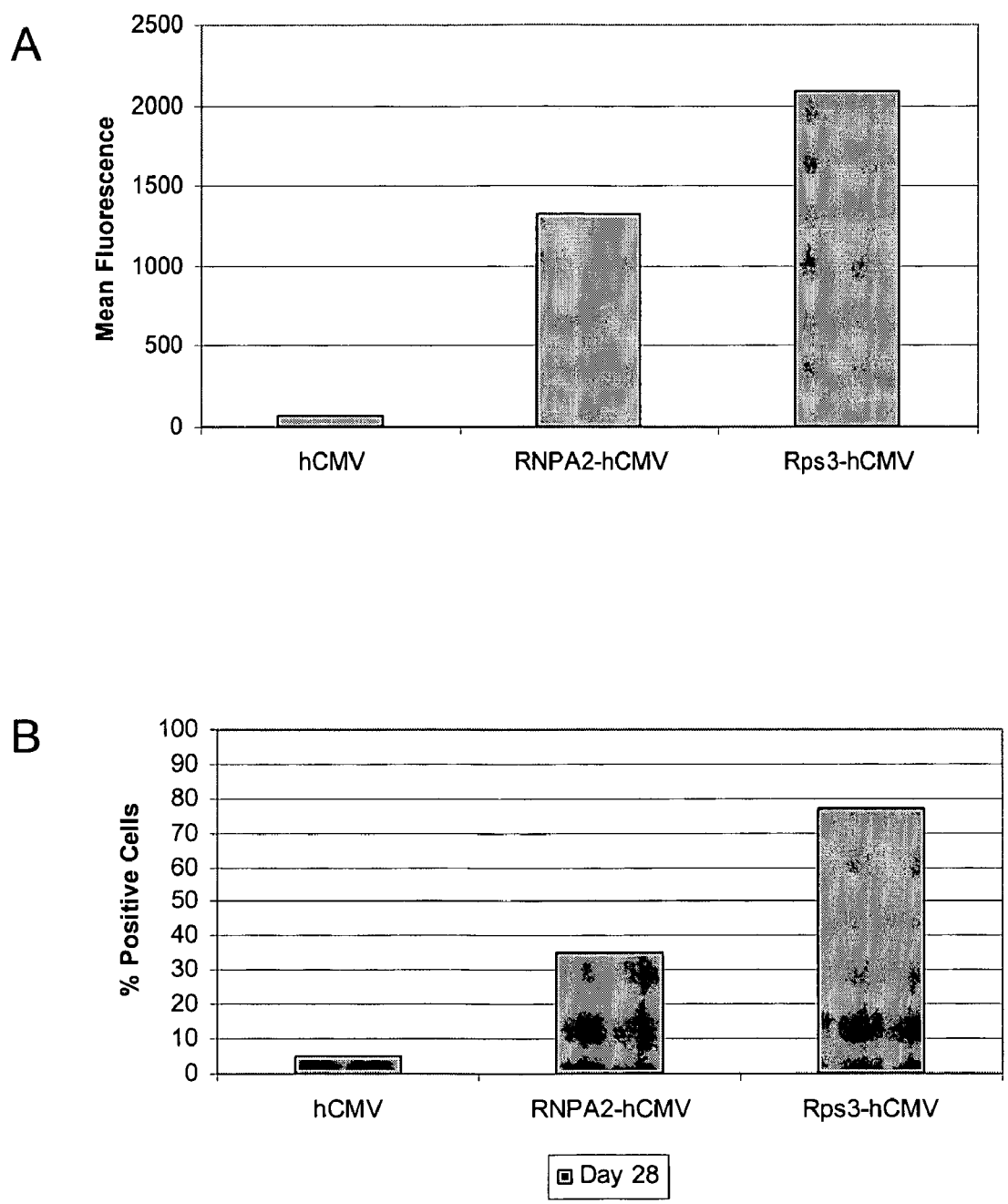
FIG. 5 shows the expression level of a reporter gene in stably transfected NSO cells when it is driven by the hCMV promoter with no additional elements present or when either an 8 kb hnRNPA2 or a 3 kb RPS3 element are placed immediately 5' to the hCMV promoter. Figure A shows the mean fluorescence intensity of the stable pools at 28 days and Figure B shows the percentage (%) positive cells.

In both CHO-K1 and NS0 cells, the percentage positive cells was significantly increased with the hnRNPA2 element but this increase was greater with the RPS3 element (FIGS. 3B and 5B)

EXAMPLE 2 rps11 Element-driven Expression

SEQ ID NO:2 shows the RPS11 cloned sequence (nucleotides 12 to 3032); SEQ ID NO:19 shows the complete sequence of pRPS11-1005-EGFP.

Rps11 containing- and control vectors (PmeI linearised) were transfected into CHO-K1 and NS0 cell lines and stable pools were generated by puromycin selection. Mean EGFP expression levels were assessed by FACscan analysis.

Figure 4:
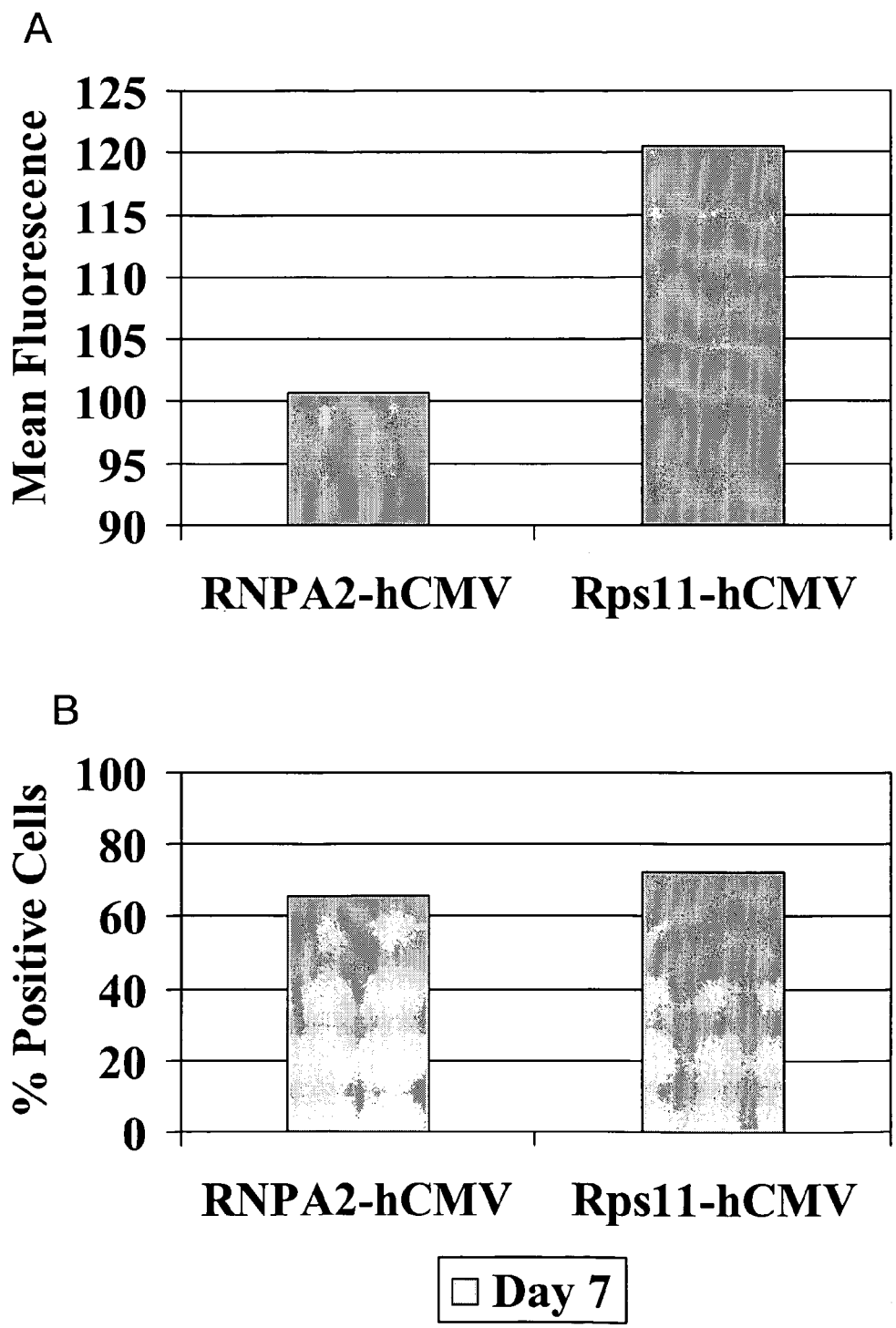
FIG. 4 shows reporter gene expression of rps11 constructs in CHO-K1 cells 7 days post-transfection (analysed by FACS). A and C are total counts, B to E are results based on just the expressing cells within the population. Figure A shows the mean fluorescence of cells in the stably selected pool, and Figure B shows percentage (%) positive cells. See Example 2.

The addition of the Rps11 element upstream of the hCMV resulted in a 1.2-fold increase in mean EGFP expression levels, in CHO-K1 pools, compared to a construct containing the previously described RNPA2 fragment (FIG. 4A).

Figure 6:
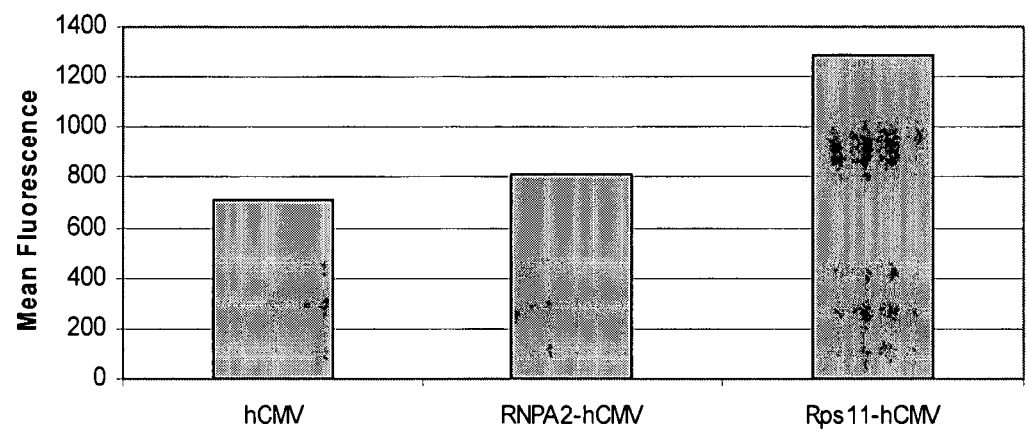
FIG. 6 shows similar data to FIG. 5 for rps 11 constructs. Figure A shows the mean fluorescence intensity values for stable pools generated with either hCMV driven constructs or identical constructs with a 8 kb hnRNPA2 or 3 kb RPS3 elements immediately 5' to the promoter. Figure B shows the percentage of cells within the pool expressing the reporter gene (percentage (%) positive cells).
Figure 6:
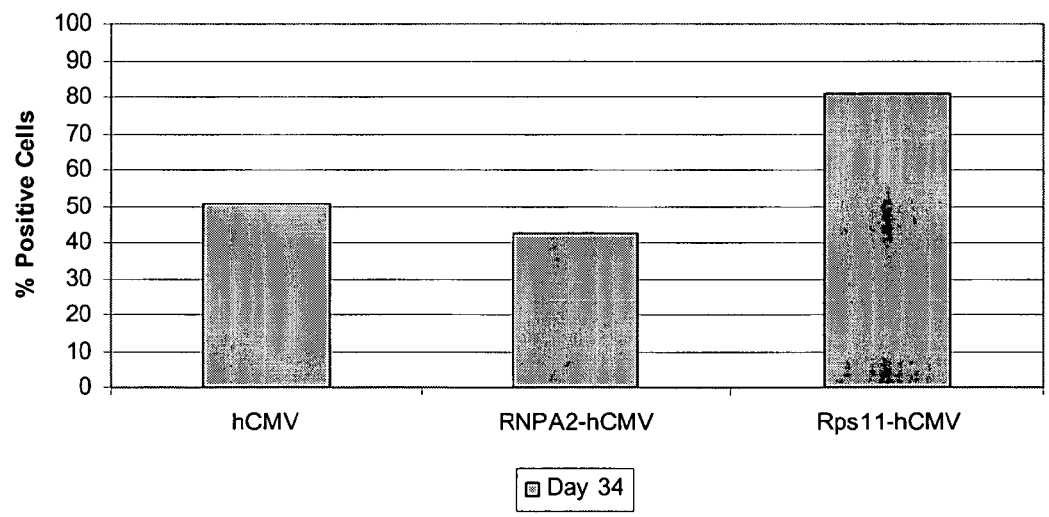

NS0 cell lines stably transfected with Rps11 containing constructs demonstated a 1.8 and 1.5 fold, (respectively) increase in mean EGFP expression levels compared to hCMV and RNPA2 constructs (FIG. 6A).

An increase in percentage positive cells was observed for CHO-K1 cell lines transfected with Rps11 constructs compared to RNPA2 constructs (FIG. 4B). Furthermore, an increase in percentage positive cells was observed in NSO pools transfected with Rps11 constructs compared to both hCMV and RNPA2 (FIG. 6B)

While the present invention has been particularly shown and described with reference to the foregoing preferred and alternative embodiments, it should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby. This description of the invention should be understood to include all novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application. Where the claims recite "a" or "a first" element of the equivalent thereof, such claims should be understood to include incorporation of one or more such elements, neither requiring nor excluding two or more such elements.

The invention claimed is:

1. An isolated polynucleotide comprising:
   a. an extended methylation-free CpG island comprising at least 300 contiguous nucleotides from the promoter region of a mammalian rps3 gene;
   b. a heterologous promoter; and
   c. a transcribable nucleic acid sequence adjacent the heterologous promoter,
   wherein the extended methylation-free CpG island is capable of increasing transcription of the transcribable nucleic acid sequence from the heterologous promoter relative to transcription in the absence of the extended methylation-free CpG island.

2. A eukaryotic expression vector comprising:
   a. an extended methylation-free CpG island from the promoter region of a mammalian rps3 gene;
   b. a heterologous promoter; and
   c. a multiple cloning site,
   wherein a transcribable nucleic acid sequence inserted into the multiple cloning site is capable of being transcribed from the heterologous promoter and the level of transcription is enhanced by the extended methylation-free CpG island relative to transcription in the absence of the extended methylation-free CpG island.

3. The polynucleotide according to claim 1, wherein the extended methylation-free CpG island comprises at least 500 contiguous nucleotides from the promoter region of the mammalian rps3 gene.

4. The polynucleotide according to claim 1, wherein the extended methylation-free CpG island comprises at least 1000 contiguous nucleotides from the promoter region of the mammalian rps3 gene.

5. The polynucleotide according to claim 1, wherein the extended methylation-free CpG island further comprises one or more exons of the mammalian rps3 gene.

6. The polynucleotide according to claim 1, wherein the mammalian rps3 gene is a human rps3 gene.

7. The polynucleotide according to claim 1, wherein the mammalian rps3 gene is a rodent rps3 gene.

8. The polynucleotide according to claim 7, wherein the rodent rps3 gene is a mouse rps3 gene.

9. The polynucleotide according to claim 8, comprising the nucleotide sequence of SEQ ID NO:1.

10. The polynucleotide according to claim 1, wherein the heterologous promoter is a constitutive promoter.

11. The polynucleotide according to claim 10, wherein the constitutive promoter is selected from the group consisting of cytomegalovirus early/immediate promoter, SV40, EF-1α, Rous sarcoma virus (RSV) LTR and HIV2 LTR.

12. The polynucleotide according to claim 11, wherein the constitutive promoter is a cytomegalovirus early/immediate promoter.

13. The polynucleotide according to claim 12, wherein the constitutive promoter is a guinea pig cytomegalovirus early/immediate promoter.

14. The polynucleotide according to claim 12, wherein the constitutive promoter is a mouse cytomegalovirus early/immediate promoter.

15. The polynucleotide according to claim 1, wherein the heterologous promoter is a tissue-selective promoter.

16. The polynucleotide according to claim 15, wherein the heterologous promoter is a tumour-selective promoter.

17. The polynucleotide according to claim 16, wherein the promoter is selected from the group consisting of carcinoembryonic antigen (CEA), prostate-specific antigen (PSA), cyclooxygenase-2 (COX-2), alpha-fetoprotein (AFP), tyrosinase, and T-cell Factors 1-4 (TCF) based promoters.

18. The polynucleotide according to claim 1, wherein the transcribable nucleic acid encodes a polypeptide selected from the group consisting of an antibody, a functional epitope-binding fragment of an antibody, a growth factor, a cytokine, a protein kinase, a soluble receptor, a membrane-bound receptor and a blood clotting factor.

19. A vector comprising of the polynucleotide of claim 18.

20. The vector according to claim 19, wherein the vector is eukaryotic expression vector.

21. A host cell comprising the polynucleotide of claim 1 or the vector of claim 2.

22. The host cell according to claim 21, wherein the cell is selected from the group consisting of CHO, NS0, BHK, HeLa and HepG2.

23. A method of increasing the percentage of host cells expressing a polypeptide encoded by a polynucleotide with which said cells are transfected comprising:
   a. transfecting a population of cells with an isolated polynucleotide according to claim 1, wherein the transcribable polynucleotide encodes a polypeptide; and
   b. measuring the number of host cells which express the polypeptide, wherein an increase in the number of cells expressing the polypeptide relative to the cells expressing the polypeptide by a polynucleotide lacking an extended methylation-free CpG island is an indication that the percentage of host cells expressing the polypeptide is increased.

24. The method according to claim 23, wherein the polypeptide is an antibody or a functional epitope-binding fragment thereof.

25. The eukaryotic expression vector according to claim 2, wherein the transcribable nucleic acid encodes an antibody or a functional epitope-binding fragment of an antibody.

26. A method of expressing a polypeptide encoded by a transcribable nucleic acid comprising inserting an expression vector according to claim 2 or claim 25 into an appropriate host cell and culturing the host cell under conditions to allow expression of the polypeptide.

27. An isolated polynucleotide comprising:
a. an extended methylation-free CpG island comprising the nucleotide sequence set forth in SEQ ID NO:1;
b. a heterologous promoter; and
c. a transcribable nucleic acid sequence adjacent the heterologous promoter,
wherein the transcribable nucleic acid sequence is transcribed from the heterologous promoter and transcription is enhanced by the extended methylation-free CpG island relative to transcription in the absence of the extended methylation-free GpG island.

* * * * *

SEQUENCE LISTING

```
<160> NUMBER OF SEQ ID NOS: 20

<210> SEQ ID NO 1
<211> LENGTH: 3145
<212> TYPE: DNA
<213> ORGANISM: Mus musculus rps3

<400> SEQUENCE: 1
ctagtaacgg ccgccagtgt gctggaattc gcccttataa ccactgagcc atctctccag      60
ccctgagtca tgattttagt gtgagaggca tcattgaatt ttctgagcac ggccatcagg     120
gtagctggca caggtcttca gatacaagga gatagttata agaaggcagc catggctgtg     180
gtgcactaga aatggagaaa cagcttcatc aggtgacaga ccagtctgac tctgtcccat     240
gattagaagc catcttgtta caaggtcaaa ataagttcat tcctgttttc tgtaacactt     300
gggtttgatc ctgtcgtcaa cccatttct ggaatttgac atgttccata ctccattata     360
ccctgacttc caccctgata agatgttctg ccaagttcct gtgtagccaa cattccctg     420 gaaatctctc ttcccttgga aaccacctag tcttagaaat tttgagttat ataaattcca     480
cttctatgtt tgatgctatt ctttaaaact ccactttagg gagatagccc tgtctgatag     540
aaaataaaac ttgcttaatt tgtctaaaag agtttaagta atagttttta cttttgttcc     600
gtgggattaa tacagggtga aacagactcc cgtgtttcca gtgtgaagtg agccacacac     660
tgcagtacaa gttatatcag caggttctgc ctctgggcaa tgaactttg cttgtgtgga     720 catcagggtc tgtgtgaagg gaaggtccta tggcctagat ttatactatt caacagtctg     780
tccccgaagc cctggtgctt tattattttg acaagcccct gctgctggta ttccaccctg     840
ctgcgagtca aaaagttcc tgtctcggaa aaacaaaaca aaacaaaaca accaaaaaat     900 aaaattttt tttcccacag gttctagtgg aggtgctcac taccagaaat cctacaaata     960
agcccatctc atggatcagg gtttaccttt gtaataatat taaatctgtg tgcatgtgcg    1020
cacgcatgtg ttttatgctt gcatatatgt atacgcagcc atggttttct actgtcccac    1080
tcactctgta acttactgag ccatccagct ggtcctctaa atacatttca atgaaagttt    1140
tcattagcgt gaacgtgaag gtggtaaaat ctgttagtgt gtgcttatgc ctgtggtttg    1200
cacctctagt ctgaaggttg ctcttttcaa attttttatt tatttacgtt tttactttg    1260 agtcagaaac tcataaaggc caagctggcc tcgaattcgc tatgtagtca atgatgacct    1320
taaacttgtg accctctact tcgttagtgc tggaaccca agcttgctga gtacagagca    1380
ctttcagacc ggaactagat gtctacttcc tgttccgcct acattacagg ttgctaggtt    1440
```

```
acacccccc  tacgccgttt  tagacgcaaa  acttcatttc  ccatgcaaaa  cttcatttcc   1500
catgaacact  tgcaagggtc  gccgcgctgc  gcggcgtcat  tgctcccgcc  ctatatacct   1560
acttccgccc  gcgagccact  tcctttcctt  tcagcggcgc  gcggctgcaa  gatggcggtg   1620
cagatttcca  agaagaggaa  ggtaagcgtc  tgggcccggt  tcgggagtcc  gccgcgggtt   1680
ctacaagtgc  cagggaggcc  tgtggctccg  tgatcagtcc  tgtggagcgt  ctggggccgc   1740
ctgccgtctc  ttcgagcctc  ggatggccgt  agattgtgta  ttgggccgga  gccgggcgag   1800
tgctgtgtgc  ctgggcaagg  gagggacaaa  ctcctcgagt  tctggaccga  ctcgaacacc   1860
gggcgcctcc  agttccggac  tagacacctt  tgagcgtttc  ttggtctcca  taatagtaat   1920
cctgtggcac  agttagaggg  cgtgtgccat  cagatctagt  ccagtttctt  tagtaagtga   1980
agtttagcag  tcccttctct  tagtcgcgtg  atcctgcaag  tggccatagt  tgaaagccta   2040
cttactgact  gctgccgtgt  tcactcggga  cccggagctg  cagcgtccct  gtggttatca   2100
tttcatgggg  gaaaagtgtg  caggttgcca  ggtttagaaa  tagatggtct  gtcgtttgtg   2160
cttatgcaca  cagatgataa  acctgttttg  agtcaggatt  cctctcctat  ccgaggtaca   2220
acttacagtc  ccagctgtac  atgtgctact  tggagacaga  ttttctttg   tctcttgggt   2280 gtagattatg  ccgtagagcc  cttcgatgaa  gaggtgatga  cgagtctgag  taggaagtgt   2340
tgtctttgtc  caagatgcct  cactatgctg  cgttctgtgg  cacagctgaa  agcactgtgg   2400
tcaaaagaaa  cttcctaaag  atgaccaaga  ggcatttgtc  tgagaagggt  tgctgctttt   2460
ctgtagggcc  attgggcttg  ctctgactaa  ccctgtcttc  acctcagagg  taacttgttt   2520
cctttggttc  agtttgtagc  tgatggcatc  ttcaaagctg  agctgaatga  atttctcact   2580
cgggagctgg  ctgaagatgg  ctactctgga  gttgaagtcc  gagttacacc  aaccaggaca   2640
gaaatcatta  ttttagccac  caggtagaaa  taccattgat  tgtcacctgt  aaatactgtg   2700
tgtactgaga  tgctgtgtaa  acttgggcca  accaagcagt  aaatctgcc   tcagtgggtg   2760 taactgcttt  gttagaactg  catttgggaa  gaacttacct  tccatttaac  gtgtgtgctg   2820
gcgttgtggt  gggcggcagg  tgggatcttg  agtaaatggt  tgcgcttccc  ctctacagga   2880
cacagaatgt  tcttggggag  aagggtcgtc  ggatcagaga  gttgaccgca  gttgtccaga   2940
agcgctttgg  cttccctgaa  ggcagcgtag  aggtgagttc  ctctgcttta  tctcccgggg   3000
gttttagact  gagttgggat  gtggcttctg  ctatagaatt  gtacttctga  aaacctgaca   3060
tggccagtga  cagtcacagg  tacttgatgc  tctgagggcg  aattctgcag  atatccatca   3120
cactggcggc  cgctcgagca  tgcat                                           3145

<210> SEQ ID NO 2
<211> LENGTH: 3039
<212> TYPE: DNA
<213> ORGANISM: Mus musculus rps11

<400> SEQUENCE: 2
aattcgccct  taagactgtt  tgcctcatgc  ctgcctggcc  tgcccttcct  ccgccgccaa     60
ctagggaagt  ggggaccaaa  ggttccttag  gcactgctcc  tgtgggtaga  ggggacatta    120
gagagctgac  agcgcaccac  ctgcatgagt  ttttattaaa  gtgcaaacca  tgggatgaat    180
cagttgagct  tcagtgttga  aaatgagtag  cagggctgcc  ccacccacct  gaccaagtac    240
cctattctgc  agctatgaaa  atgagatctg  cacatgagct  ggggttcaca  agtgcacact    300
tggagcactg  ccttgctcct  tcccagcaga  ccacaaagca  gtattttcct  ggaggatttt    360
atgtgctaat  aaaattatttg  acttaagtgt  gtacgatgtg  tgctgtgcag  agaggggcag    420
```

```
agggcaccag caggtcatct gcatgggggg ccccttggg tgaatccttg ctcacgggat      480
aggctttgtt gctcaaaagt tgcagatata catcttgggt cctgtcctag atggtgttac      540
tgtaagtcag caccaagata caagagctgg tacctggact gtaggaggtc aggccatgac      600
acaaaggctg ggactaaagg catttaccac gcctgagtct tctggttctt taaacatcaa      660
atccttccgg gggctggcga gatggctcag tggttaagag cacagactgc tcttacgaag      720
gatccgagtt caaatcccag caaccaaatg gtgcctaaca actatccata tgaaatctg       780 atgccctctt ctggagtatc tgagaacagc tacagtgtac ttacatataa tcttaaaaat      840
gcttcccatg ttaaccacca ctagagtttt tattacagct agctgacctg aagccaagt       900 ccttatgcct ccgtgagtgc tggggttaaa aagatccagc accactcaaa atgtcaatct      960 atttgaaaa  tatgctttat actgttctag cccatctgtg cagggctaga acggtgaata     1020
cgagaaactg acacaagctt ttgccacctg gctaaatggt tcctctatta cctggggtgg     1080
tcacctaagg ttagacactc atccacgagt agtcaggaca taaacccatc aaagtgtggg     1140
tagacgcgca gcctgagata ctgtcaacaa aggacatgcg accttggtga cgtcggcctt     1200
taataaaagg aagaaaggtt gactattcgg tcgacgctgg ctgctcctga catcgtatgg     1260
cagatactct gctgtaaagc ggttcacccc tttcttgaga cccgctctgc acggccgctt     1320
ctctctggaa actgaatccc agcacgtgtt tcccaacccg tacggcacgc cttctccgcc     1380
ctaagcctcg ccgtaccaca tgatgcacgt ttcctccaca tcgtgctcct gaaatctcgc     1440
gagatgatag gatcttcccg ccccttagtc ctcccccgtc atggcggcgt acggacagtc     1500
ccaggaacgc gggctctcgc cggaagtacc tcccacctcc gtgaggataa ccccgcgtca     1560
cttccgcccc gacctcgcgt ggtgaataag gaagccggga gcggccctgc ctctcccttt     1620
ctccggcggc cggaagatg  gcggacattc aggttcgagc gtttagttgc ttccccccga     1680
cgcttcggtg tggagcgtat cccttggcgt cctcgttgtc ttacgcatta gctgaagcga     1740
ggatgcctgc gaatgccttc gtctcaggcg gctcggaaat ccgggctcta cgcagtaatg     1800
gggtccctgg cgcttcggga gttggttctt aaagctcaga gcttaacggg tgagggattg     1860
tggcgggagg agggcatcct gcggcgcggg agtcctgcgg cggcagagcc ggggacactg     1920
ggtaaagcag gtttttccc cttgatggag actgaggccc ggacctcgtg cgctctacgg      1980
cagggctgcg gtcccgacct cgctgtagtt ttcagtgtga gcgcagctct ggcctcgatg     2040
agcttaggct tgtcttaaac ttgccatcct gcctcaacct caaccgggat gacagatccg     2100
gcccaccagg ctcggctacg tggacataag cttgaatccc gaatgagtgg atttgtatgt     2160
tttggaggtc cagtctggct gaaaagctct ttttgatctc agccgtgagt tctgcaggct     2220
gtggaggtgt tagatgggac gcagtgtgtg agctaaacta gacttggggt ggttggagag     2280
ccctgaccag ccggttttgg cgattggggc aaataaggtt gaaggtagga aggaagaaat     2340
attgtctctg atttccttga actttacctg caacctcacc aaattctcat ccctacagac     2400
ggagcgtgct taccaaaagc agcctacgat cttcaaaac aagaagcggg ttctgctggg      2460
agaaaccggc aaggaaaaac tccctcggta ctacaagaat atcggtctag cttcaagac      2520 gcctaaagag gtacaggacc ctccagcaga tgagatccct gctgccctgc acgtgtggga     2580
gcacagccac cccgccccct tcacagtggc ttccatggg  ccctgggaa ttgtagtatg      2640 ggccctgagg cgtcatcctt ggttctgttt aggaagtggt aatctaaacc ccactttctt     2700
aactttgcag gctattgagg gtacctacat agacaagaaa tgccccttca ctggtaacgt     2760
```

```
ctccatccga ggtcggatcc tgtctggtga gtgggatgtt ggaagggtgg ttctaggttc    2820
ctgcgtccag gggcgctggc aagtgatgtc tgttctcacg atggtcttca gatgtcctct    2880
agggcactgc tgagacagcc agttgacaaa gctgatgcca taaatggagc ttcttgggag    2940
ccccgttcaa ctgactccta cctgctaaca cctttctgtt actctcccag gtgtcgtgac    3000
gaagatgaag atgcagagga ccattgtcat ccaagggcg                           3039
```

```
<210> SEQ ID NO 3
<211> LENGTH: 22
<212> TYPE: DNA
<213> ORGANISM: Artificial
<220> FEATURE:
<223> OTHER INFORMATION: Synthetic PCR oligonucleotide

<400> SEQUENCE: 3
gtagtttctg acttggaaat gt                                              22

<210> SEQ ID NO 4
<211> LENGTH: 21
<212> TYPE: DNA
<213> ORGANISM: Artificial
<220> FEATURE:
<223> OTHER INFORMATION: Synthetic PCR oligonucleotide

<400> SEQUENCE: 4
aactgacctg ccatgccatt c                                               21

<210> SEQ ID NO 5
<211> LENGTH: 19
<212> TYPE: DNA
<213> ORGANISM: Artificial
<220> FEATURE:
<223> OTHER INFORMATION: Synthetic PCR oligonucleotide

<400> SEQUENCE: 5
gagcagtccg gtgtcacta                                                  19

<210> SEQ ID NO 6
<211> LENGTH: 21
<212> TYPE: DNA
<213> ORGANISM: Artificial
<220> FEATURE:
<223> OTHER INFORMATION: Synthetic PCR oligonucleotide

<400> SEQUENCE: 6
gcagagaagc agacagttat g                                               21

<210> SEQ ID NO 7
<211> LENGTH: 21
<212> TYPE: DNA
<213> ORGANISM: Artificial
<220> FEATURE:
<223> OTHER INFORMATION: Synthetic PCR oligonucleotide

<400> SEQUENCE: 7
cagagcatca agtacctgtg a                                               21

<210> SEQ ID NO 8
<211> LENGTH: 21
<212> TYPE: DNA
<213> ORGANISM: Artificial
<220> FEATURE:
<223> OTHER INFORMATION: Synthetic PCR oligonucleotide

<400> SEQUENCE: 8
```

-continued taaccactaa gccatctctc c                                            21

<210> SEQ ID NO 9
<211> LENGTH: 20
<212> TYPE: DNA
<213> ORGANISM: Artificial
<220> FEATURE:
<223> OTHER INFORMATION: Synthetic PCR oligonucleotide

<400> SEQUENCE: 9
caagaacaag gaagctggcc                                              20

<210> SEQ ID NO 10
<211> LENGTH: 22
<212> TYPE: DNA
<213> ORGANISM: Artificial
<220> FEATURE:
<223> OTHER INFORMATION: Synthetic PCR oligonucleotide

<400> SEQUENCE: 10
taaaacccac agcactgtag gg                                           22

<210> SEQ ID NO 11
<211> LENGTH: 20
<212> TYPE: DNA
<213> ORGANISM: Artificial
<220> FEATURE:
<223> OTHER INFORMATION: Synthetic PCR oligonucleotide

<400> SEQUENCE: 11
aagactgttt gcctcatgcc                                              20

<210> SEQ ID NO 12
<211> LENGTH: 20
<212> TYPE: DNA
<213> ORGANISM: Artificial
<220> FEATURE:
<223> OTHER INFORMATION: Synthetic PCR oligonucleotide

<400> SEQUENCE: 12
ggatgacaat ggtcctctgc                                              20

<210> SEQ ID NO 13
<211> LENGTH: 20
<212> TYPE: DNA
<213> ORGANISM: Artificial
<220> FEATURE:
<223> OTHER INFORMATION: Synthetic PCR oligonucleotide

<400> SEQUENCE: 13
gtggttgtag gttcacgtcc                                              20

<210> SEQ ID NO 14
<211> LENGTH: 20
<212> TYPE: DNA
<213> ORGANISM: Artificial
<220> FEATURE:
<223> OTHER INFORMATION: Synthetic PCR oligonucleotide

<400> SEQUENCE: 14
atccctcaca ttgccaagcc                                              20

<210> SEQ ID NO 15
<211> LENGTH: 20
<212> TYPE: DNA

```
<213> ORGANISM: Artificial
<220> FEATURE:
<223> OTHER INFORMATION: Synthetic PCR oligonucleotide

<400> SEQUENCE: 15
acttaagacc tgatgcctcc                                                  20

<210> SEQ ID NO 16
<211> LENGTH: 20
<212> TYPE: DNA
<213> ORGANISM: Artificial
<220> FEATURE:
<223> OTHER INFORMATION: Synthetic PCR oligonucleotide

<400> SEQUENCE: 16
gctagcttac ataggcagcc                                                  20

<210> SEQ ID NO 17
<211> LENGTH: 8691
<212> TYPE: DNA
<213> ORGANISM: Artificial
<220> FEATURE:
<223> OTHER INFORMATION: Vector pRPS3 1005 EGFP

<400> SEQUENCE: 17
cgttgtaaaa cgacggccag tgaattgtaa tacgactcac tatagggcga attgggtacc        60
gggccccccc tcgaagttta acatttaaa tctagtaacg gccgccagtg tgctggaatt       120
cgcccttata accactgagc catctctcca gccctgagtc atgattttag tgtgagaggc       180
atcattgaat tttctgagca cggccatcag ggtagctggc acaggtcttc agatacaagg       240
agatagttat aagaaggcag ccatggctgt ggtgcactag aaatggagaa acagcttcat       300
caggtgacag accagtctga ctctgtccca tgattagaag ccatcttgtt acaaggtcaa       360
aataagttca ttcctgtttt ctgtaacact tgggtttgat cctgtcgtca acccattttc       420
tggaatttga catgttccat actccattat accctgactt ccaccctgat aagatgttct       480
gccaagttcc tgtgtagcca acattcccct ggaaatctct cttcccttgg aaaccaccta       540
gtcttagaaa ttttgagtta tataaattcc acttctatgt ttgatgctat tctttaaaac       600
tccactttag ggagatagcc ctgtctgata gaaaataaaa cttgcttaat ttgtctaaaa       660
gagtttaagt aatagttttt acttttgttc cgtgggatta atacagggtg aaacagactc       720
ccgtgtttcc agtgtgaagt gagccacaca ctgcagtaca agttatatca gcaggttctg       780
cctctgggca atgaactttt gcttgtgtgg acatcagggt ctgtgtgaag ggaaggtcct       840
atggcctaga tttatactat tcaacagtct gtccccgaag ccctggtgct ttattatttt       900
gacaagcccc tgctgctggt attccaccct gctgcgagtc aaaaaagttc ctgtctcgga       960
aaaacaaaac aaaacaaaac aaccaaaaaa taaaattttt ttttcccaca ggttctagtg      1020
gaggtgctca ctaccagaaa tcctacaaat aagcccatct catggatcag ggtttacctt      1080
tgtaataata ttaaatctgt gtgcatgtgc gcacgcatgt gttttatgct tgcatatatg      1140
tatacgcagc catggttttc tactgtccca ctcactctgt aacttactga gccatccagc      1200
tggtcctcta aatacatttc aatgaaagtt tcattagcg tgaacgtgaa ggtggtaaaa       1260
tctgttagtg tgtgcttatg cctgtggttt gcacctctag tctgaaggtt gctcttttca      1320
aattttttat ttatttacgt ttttactttt gagtcagaaa ctcataaagg ccaagctggc      1380
ctcgaattcg ctatgtagtc aatgatgacc ttaaacttgt gaccctctac ttcgttagtg      1440
ctggaacccc aagcttgctg agtacagagc actttcagac cggaactaga tgtctacttc      1500
```

-continued

```
ctgttccgcc tacattacag gttgctaggt tacaccccc ctacgccgtt ttagacgcaa      1560
aacttcattt cccatgcaaa acttcatttc ccatgaacac ttgcaagggt cgccgcgctg      1620
cgcggcgtca ttgctcccgc cctatatacc tacttccgcc cgcgagccac ttcctttcct      1680
ttcagcggcg cgcggctgca agatggcggt gcagatttcc aagaagagga aggtaagcgt      1740
ctgggcccgg ttcgggagtc cgccgcgggt tctacaagtg ccaggaggc ctgtggctcc      1800 gtgatcagtc ctgtggagcg tctggggccg cctgccgtct cttcgagcct cggatggccg      1860
tagattgtgt attgggccgg agccgggcga gtgctgtgtg cctgggcaag ggagggacaa      1920
actcctcgag ttctggaccg actcgaacac cgggcgcctc cagttccgga ctagacacct      1980
ttgagcgttt cttggtctcc ataatagtaa tcctgtggca cagttagagg gcgtgtgcca      2040
tcagatctag tccagtttct ttagtaagtg aagtttagca gtcccttctc ttagtcgcgt      2100
gatcctgcaa gtggccatag ttgaaagcct acttactgac tgctgccgtg ttcactcggg      2160
acccggagct gcagcgtccc tgtggttatc atttcatggg ggaaaagtgt gcaggttgcc      2220
aggtttagaa atagatggtc tgtcgtttgt gcttatgcac acagatgata aacctgtttt      2280
gagtcaggat tcctctccta tccgaggtac aacttacagt cccagctgta catgtgctac      2340
ttggagacag attttctttt gtctcttggg tgtagattat gccgtagagc ccttcgatga      2400
agaggtgatg acgagtctga gtaggaagtg ttgtctttgt ccaagatgcc tcactatgct      2460
gcgttctgtg gcacagctga aagcactgtg gtcaaaagaa acttcctaaa gatgaccaag      2520
aggcatttgt ctgagaaggg ttgctgcttt tctgtagggc cattgggctt gctctgacta      2580
accctgtctt cacctcagag gtaacttgtt cctttggtt cagtttgtag ctgatggcat      2640
cttcaaagct gagctgaatg aatttctcac tcgggagctg gctgaagatg gctactctgg      2700
agttgaagtc cgagttacac caaccaggac agaaatcatt attttagcca ccaggtagaa      2760
ataccattga ttgtcacctg taaatactgt gtgtactgag atgctgtgta aacttgggcc      2820
aaccaagcag taaatctggc ctcagtgggt gtaactgctt tgttagaact gcatttggga      2880
agaacttacc ttccatttaa cgtgtgtgct ggcgttgtgg tgggcggcag gtgggatctt      2940
gagtaaatgg ttgcgcttcc cctctacagg acacagaatg ttcttgggga aagggtcgt       3000 cggatcagag agttgaccgc agttgtccag aagcgctttg gcttccctga aggcagcgta      3060
gaggtgagtt cctctgcttt atctcccggg ggttttagac tgagttggga tgtggcttct      3120
gctatagaat tgtacttctg aaaacctgac atggccagtg acagtcacag gtacttgatg      3180
ctctgagggc gaattctgca gatatccatc acactggcgg ccgctcgagc atgcatctag      3240
aagcttatcg ataccggtgg cgcgccaatt gaattaagat ctggcccaat gggccgtacg      3300
aattcgagct cggtacccgg ggatcctgat ctaatagtaa tcaattacgg ggtcattagt      3360
tcatagccca tatatggagt tccgcgttac ataacttacg gtaaatggcc cgcctggctg      3420
accgcccaac gacccccgcc cattgacgtc aataatgacg tatgttccca tagtaacgcc      3480
aatagggact ttccattgac gtcaatgggt ggagtattta cggtaaactg cccacttggc      3540
agtacatcaa gtgtatcata tgccaagtac gccccctatt gacgtcaatg acggtaaatg      3600
gcccgcctgg cattatgccc agtacatgac cttatgggac tttcctactt ggcagtacat      3660
ctacgtatta gtcatcgcta ttaccatggt gatgcggttt tggcagtaca tcaatgggcg      3720
tggatagcgg tttgactcac ggggatttcc aagtctccac cccattgacg tcaatgggag      3780
tttgttttgg caccaaaatc aacgggactt tccaaaatgt cgtaacaact ccgccccatt      3840
```

```
gacgcaaatg ggcggtaggc gtgtacggtg ggaggtctat ataagcagag ctggtttagt    3900
gaaccgtcag atccgtcgcc accatggtga gcaagggcga ggagctgttc accggggtgg    3960
tgcccatcct ggtcgagctg gacggcgacg taaacggcca aagttcagc gtgtccggcg     4020
agggcgaggg cgatgccacc tacggcaagc tgaccctgaa gttcatctgc accaccggca    4080
agctgcccgt gccctggccc accctcgtga ccacctgac ctacggcgtg cagtgcttca     4140
gccgctaccc cgaccacatg aagcagcacg acttcttcaa gtccgccatg cccgaaggct    4200
acgtccagga gcgcaccatc ttcttcaagg acgacggcaa ctacaagacc cgcgccgagg    4260
tgaagttcga gggcgacacc ctggtgaacc gcatcgagct gaagggcatc gacttcaagg    4320
aggacggcaa catcctgggg cacaagctgg agtacaacta caacagccac aacgtctata    4380
tcatggccga caagcagaag aacggcatca aggtgaactt caagatccgc cacaacatcg    4440
aggacggcag cgtgcagctc gccgaccact accagcagaa cacccccatc ggcgacggcc    4500
ccgtgctgct gcccgacaac cactacctga gcacccagtc cgccctgagc aaagaccca    4560
acgagaagcg cgatcacatg gtcctgctgg agttcgtgac cgccgccggg atcactctcg    4620
gcatggacga gctgtacaag taaagcggcc gcgactctag atcataatca gccataccac    4680
atttgtagag gttttacttg ctttaaaaaa cctcccacac ctccccctga acctgaaaca    4740
taaaatgaat gcaattgttg ttgttaactt gtttattgca gcttataatg gttacaaata    4800
aagcaatagc atcacaaatt tcacaaataa agcatttttt tcactgcatt ctagttgtgg    4860
tttgtccaaa ctcatcaatg tatcttaact agagtcgacc tgcaggcatg caagcttacc    4920
ggtggcgcgc gcgccaattg ttaattaaga tctggcccaa tgggccgtac gaattcctta    4980
ggctaccggg tagggaggc gcttttccca aggcagtctg gagcatgcgc tttagcagcc    5040
ccgctgggca cttggcgcta cacaagtggc ctctggcctc gcacacattc cacatccacc    5100
ggccggtagg cgccaaccgg ctccgttctt tggtggcccc ttcgcgccac cttctactcc    5160
tcccctagtc aggaagttcc cccccgcccc gcagctcgcg tcgtgcagga cgtgacaaat    5220
ggaagtagca cgtctcacta gtctcgtgca gatggacagc accgctgagc aatggaagcg    5280
ggtaggcctt tggggcagcg gccaatagca gctttgctcc ttcgctttct gggctcagag    5340
gctgggaagg ggtgggtccg ggggcgggct caggggcggg ctcaggggcg ggcgggcgc    5400
ccgaaggtcc tccggaggcc cggcattctg cacgcttcaa aagcgcacgt ctgccgcgct    5460
gttctcctct tcctcatctc cgggcctttc gaccagctta ccatgaccga gtacaagccc    5520
acggtgcgcc tcgccacccg cgacgacgtc cccagggccg tacgcaccct cgccgccgcg    5580
ttcgccgact accccgccac gcgccacacc gtcgatccgg accgccacat cgagcgggtc    5640
accgagctgc aagaactctt cctcacgcgc gtcgggctcg acatcggcaa ggtgtgggtc    5700
gcggacgacg gcgccgcggt ggcggtctgg accacgccgg agagcgtcga agcggggcg    5760
gtgttcgccg agatcggccc gcgcatggcc gagttgagcg gttcccggct ggccgcgcag    5820
caacagatgg aaggcctcct ggcgccgcac cggcccaagg agcccgcgtg gttcctggcc    5880
accgtcggcg tctcgcccga ccaccagggc aagggtctgg gcagcgccgt cgtgctcccc    5940
ggagtggagg cggccgagcg cgccggggtg cccgccttcc tggagacctc gcgccccgc    6000
aacctccccct tctacgagcg gctcggcttc accgtcaccg ccgacgtcga ggtgcccgaa    6060
ggaccgcgca cctggtgcat gaccgcaag cccggtgcct gacgcccgcc ccacgacccg    6120
cagcgcccga ccgaaggag cgcacgaccc catgcatcgt agacgaaatg accgaccaag    6180
cgacgcccaa cctgccatca cgagatttcg attccaccgc cgccttctat gaaaggttgg    6240
```

```
gcttcggaat cgttttccgg gacgccggct ggatgatcct ccagcgcggg gatctcatgc   6300
tggagttctt cgcccaccct aggggaggc taactgaaac acggaaggag acaataccgg    6360
aaggaacccg cgctatgacg gcaataaaaa gacagaataa aacgcacggt gttgggtcgt   6420
ttgttcataa acgcggggtt cggtcccagg gctggcactc tgtcgatacc ccaccgagac   6480
cccattgggg ccaatacgcc cgcgtttctt ccttttcccc accccacccc caagttcgg    6540 gtgaaggccc agggctcgca gccaacgtcg gggcggcagg cccccagctt tgttcccctt   6600
tagtgagggt taatttcgag cttggcgtaa tcatggtcat agctgttttcc tgtgtgaaat   6660 tgttatccgc tcacaattcc acacaacata cgagccggaa gcataaagtg taaagcctgg   6720
ggtgcctaat gagtgagcta actcacatta attgcgttgc gctcactgcc cgctttccag   6780
tcgggaaacc tgtcgtgcca gcatcgcgag cacttttcgg ggaaatgtgc gcggaacccc   6840
tatttgttta ttttttctaaa tacattcaaa tatgtatccg ctcatgagac aataaccctg   6900
ataaatgctt caataatatt gaaaaggaa gagtatgagt attcaacatt tccgtgtcgc    6960
ccttattccc ttttttgcgg catttttgcct tcctgttttt gctcacccag aaacgctggt   7020
gaaagtaaaa gatgctgaag atcagttggg tgcacgagtg ggttacatcg aactggatct   7080
caacagcggt aagatccttg agagttttcg ccccgaagaa cgttttccaa tgatgagcac   7140
ttttaaagtt ctgctatgtg gcgcggtatt atcccgtatt gacgccgggc aagagcaact   7200
cggtcgccgc atacactatt ctcagaatga cttggttgag tactcaccag tcacagaaaa   7260
gcatcttacg gatggcatga cagtaagaga attatgcagt gctgccataa ccatgagtga   7320
taacactgcg gccaacttac ttctgacaac gatcggagga ccgaaggagc taaccgcttt   7380
tttgcacaac atgggggatc atgtaactcg ccttgatcgt tgggaaccgg agctgaatga   7440
agccatacca aacgacgagc gtgacaccac gatgcctgta gcaatggcaa caacgttgcg   7500
caaactatta actggcgaac tacttactct agcttcccgg caacaattaa tagactggat   7560
ggaggcggat aaagttgcag gaccacttct gcgctcggcc cttccggctg gctggtttat   7620
tgctgataaa tctggagccg gtgagcgtgg gtctcgcggt atcattgcag cactggggcc   7680
agatggtaag ccctcccgta tcgtagttat ctacacgacg gggagtcagg caactatgga   7740
tgaacgaaat agacagatcg ctgagatagg tgcctcactg attaagcatt ggtaactgtc   7800
agactcgcga cactgcatta atgaatcggc caacgcgcgg ggagaggcgg tttgcgtatt   7860
gggcgctctt ccgcttcctc gctcactgac tcgctgcgct cggtcgttcg gctgcggcga   7920
gcggtatcag ctcactcaaa ggcggtaata cggttatcca cagaatcagg ggataacgca   7980
ggaaagaaca tgtgagcaaa aggccagcaa aaggccagga accgtaaaaa ggccgcgttg   8040
ctggcgtttt tccataggct ccgcccccct gacgagcatc acaaaaatcg acgctcaagt   8100
cagaggtggc gaaacccgac aggactataa agataccagg cgtttccccc tggaagctcc   8160
ctcgtgcgct ctcctgttcc gaccctgccg cttaccggat acctgtccgc ctttctccct   8220 tcggaagcg tggcgctttc tcatagctca cgctgtaggt atctcagttc ggtgtaggtc   8280
gttcgctcca agctgggctg tgtgcacgaa ccccccgttc agcccgaccg ctgcgcctta   8340
tccggtaact atcgtcttga gtccaacccg gtaagacacg acttatcgcc actggcagca   8400
gccactggta acaggattag cagagcgagg tatgtaggcg gtgctacaga gttcttgaag   8460
tggtggccta actacggcta cactagaagg acagtatttg gtatctgcgc tctgctgaag   8520
ccagttacct tcggaaaaag agttggtagc tcttgatccg gcaaacaaac caccgctggt   8580
```

-continued

| | |
|---|---|
| agcggtggtt tttttgtttg caagcagcag attacgcgca gaaaaaaagg atctcaagaa | 8640 |
| gatcctttga tcttttctac ggggtctgac gctcagtgga acgaaaactc a | 8691 |

<210> SEQ ID NO 18
<211> LENGTH: 13827
<212> TYPE: DNA
<213> ORGANISM: Artificial
<220> FEATURE:
<223> OTHER INFORMATION: Vector pCET 1015 EGFP

<400> SEQUENCE: 18

| | |
|---|---|
| cgttgtaaaa cgacggccag tgaattgtaa tacgactcac tatagggcga attgggtacc | 60 |
| gggccccccc tcgaagttta aacatttaaa tctagaagct tcaatgtttt tagcaccctc | 120 |
| tgtgtggagg aaaataatgc agattattct aattagtgta atatctaacc acattaaaat | 180 |
| atattacata gtaaactaca ctccataatt ttataaattt gactcccag ggtaataaac | 240 |
| tagtctctag tctgctcacc ttcaactgta caataaagtc ttggttcttt tgaaatagac | 300 |
| ctcaaatgag acacctaaaa ttcaaagtgt ctttacattt aaagacacct acaggaaagc | 360 |
| aggtaaaaga gccaggttaa aaacaaattc taaaaccact tagctgcagt taaacatata | 420 |
| gtaaagatgc actaaagttt cttactctgt aaatcccttc cacttcagga atattccac | 480 |
| tttcccattc actacacgtc gatctagtac ttttttccacg acaaattctt caggctctgc | 540 |
| ctcttcaact tttttactct ttccattctg tttttttccc attttttgct aaaataaaac | 600 |
| aaaagagaaa ttaagaaata ttcctcttga attttgagca cattttcaag gctcaattgc | 660 |
| ttatattatt atcacattcg acataaattt ttacttctat atcccagggc agacaccttc | 720 |
| tggaaagatt aaaagtcaac agacaataaa ataaaagaat gctttatctt gttcatttag | 780 |
| ttcaaactta caacccacca ccaaaataat acaataaaaa aacactatct ggaaacagtt | 840 |
| attttttttcc agtctttttt tttgagacag ggtctcacac tcttgtcgcc caggctggag | 900 |
| tgcagtggcg tgatctcagc tcactgcaac ctccgcctcc ccaggttcaa gcagttctca | 960 |
| tgcctcagcc tccagagtag ctgggattat aggcggatgc caccatgccg ggctaatttt | 1020 |
| ttttgtgttt ttattagaaa cagggtttca ccatgttgac caggctggtc tcaaactcct | 1080 |
| gacctgaagt gattcaccag cctgggcctc ccaaagtgct ggcattacag gcgtgagcca | 1140 |
| ctgcgcccgg ccctgtagtc ttaaaagacc aagtttacta attttcactc attttaacaa | 1200 |
| cactgcaaca aacaactatg caggaagtac ctaaagggtg atccagagaa gcaagtagta | 1260 |
| gtgacaggtc ttaggtgaac ctatgacaga ccttgtatcc accccagat ggtaaaagcc | 1320 |
| ccagccccct tctcaattca aatattaatg tcaaaagcat caatgataca gagaaaagat | 1380 |
| aaaatgcaga tgaaaacatg gttcaaaatc ctgataccaa ctgcagggtc aactatagag | 1440 |
| accactagga ggttcaatta aaggacaaga ttatttttcc ataatctctg tagataatat | 1500 |
| ttcctaccac ttgaacaaa actataaagc tatcacttca agagaccaac attacaaatt | 1560 |
| tattttaatt ccctaaggtg aaaaaaatcc ttccttcctg gtttctcaag agaaagtcta | 1620 |
| tactggtaac caaattcact ttaaacaggc attttctttg gtatgacact atttaagaga | 1680 |
| agcaggaaac caacgtgaac cagctctttc caatggctca agatttccta tgagaggact | 1740 |
| aaaaatgggg aaaatttta tgagaggatt aaaaatgggg gaaaaaaac cctgaaatgg | 1800 |
| ttaatcagaa gatcctatgg gctgagaagg aatccatctt aacatttcat cttaaagcaa | 1860 |
| atgctattgc cggggggcagt ggctcatgcc tgtaatccca gcactttggg aggccgaggt | 1920 |
| gggcagatca tctgaggtca ggagtttgag accagcctga ccaacatgga gaaaccccgt | 1980 |

```
ttctactaaa aatacaaaat tagccaggca tagtggtgca tgcctgtaat cccagctact   2040
tgggaggctg aggcaggaga actgcttgaa cccaggaggc ttaagttgcg gtgagccaag   2100
atcacgccat tgcactctag cctggacaac aagagaaaaa ctctgtctca aaaaacaca   2160 aaacaaaaa acccaaatac tatttaaaaa agataaacct taattgctca atcattaaag   2220
ccatcccaca agtaaagcag caagcagaaa aaagttaaga acacctcaag gctacagaag   2280
gacatttcaa gctatgcagg catatgaagt gtgcagacag atatgtaaga aaggcctcaa   2340
gactgcaaaa gggcatttca agctatgcaa gcatataggt aacacataca cacacacaaa   2400
ataaaatccc ctgaaataca aaaacatgca gcaaacacct gacgttttg gataccattt    2460 ctaagtcagg tgttatgatt ctcattagtc aagatacttg agtactgggc ccaaacagct   2520
ttctgccact gtacagtaca agaaggtagg aataatggtg ggaggagcaa agacaaactg   2580
taatagacag aagtgtatca gatacctata ctacatgaaa aacaaaacag ctactgccac   2640
aaagggagaa ggctaacaaa ataaagtcaa caataaatac agaaaatgaa aaggatacac   2700
actaaggttt acaaaaaaaa aaaggcagac aaaatgccat acagtattca ttcactacta   2760
tggcattcat aagctagttt caaatgctca ctattttctt ttatagtata tatttgcctt   2820
aacccagcac ttttttccaa aagtggatga gtcaaaataa atttcccatt atttaagtga   2880
aattaacagc acacatatct cacaacacta atgaattttt aaaatggaaa gttaagaact   2940
tttaaagtgg ccaacctgtg atccttcaca aaataaacta aatacaataa cagaccccaa   3000
aggctatcaa ttgcgtgcaa aaacaacttc tgttttccag ggtaaacaga atctaatgca   3060
gaatctaatg cagggtaaac agacttaatg cagaatctaa tgatggcaca aattaaaaat   3120
cactaacgtg ccctttttag tgtgaaaccc agagagagca catacaagcc aaaaacaaat   3180
gctttatttt acctaggaga cattaacatt caccttacg tgtttaagat taatgcaatg     3240
ttaaatattg tgaaaactgt aactttgaat ttcatgattt ttatgtgaat attccagggt   3300
ttaaaaaaac ttgtaacatg acatggctga ataagataaa aaaaaaatct agccttttct   3360
cccttctggc tcatatttgc gatttcgatc attttgttta aaaacaaaa cactgcaatg    3420 aattaaactt aatattcttc tatgttttag agtaagttaa aacaagataa agtgaccaaa   3480
gtaatttgaa agattcaatg acttttgctc caacctaggt gcacaaggta ccttgttctt   3540
taaattgggc tttaatgaaa atacttctcc agaattctgg ggatttaaga aaaattatgc   3600
caaccaacaa gggctttacc atttatgta acattttca acgctgcaaa aatgtgtgta     3660
tttctatttg aagataaaaa tcctcagcaa aatccacatt gcactgtcct tcaaagatta   3720
gccttctttg aactagttaa gacactatta agccaagcca gtatctccct gtaatgaatt   3780 cgttttctc ttaatttcc cctgtaattt acactgggag agctgggaaa tatgtggatg      3840
taaatttctc agccacagag atgcaaagtt atactgtggg gaaaaaaaac ttgagttaaa   3900
tccttacata ttttaggttt tcattaactt accaatgtag ttttgttgga ggccattttt   3960
tttattgcag acttgaagag ctattactag aaaaatgcat gacagttaag gtaagtttgc   4020
atgacacaaa aaaggtaact aaatacaaat tctgtttgga ttccaacccc caagtagaga   4080
gcgcacactt tcaaacgtga atacaaatcc agagtagatc tgcgctccta cctacattgc   4140
ttatgatgta cttaagtacg tgtcctaacc atgtgagtct agaaagactt tactggggat   4200
cctggtacct aaaacagctt cacatggctt aaaatagggg accaatgtct tttccaatct   4260
aagtcccatt tataataaag tccatgttcc attttttaaag gacaatcctt tcggtttaaa   4320
```

```
accaggcacg attacccaaa caactcacaa cggtaaagca ctgtgaatct tctctgttct    4380
gcaatcccaa cttggtttct gctcagaaac cctccctctt tccaatcggt aattaaataa    4440
caaaaggaaa aaacttaaga tgcttcaacc ccgtttcgtg acactttgaa aaaagaatca    4500
cctcttgcaa acacccgctc ccgacccccg ccgctgaagc ccggcgtcca gaggcctaag    4560
cgcgggtgcc cgcccccacc cgggagcgcg ggcctcgtgg tcagcgcatc cgcggggaga    4620
aacaaaggcc gcggcacggg ggctcaaggg cactgcgcca caccgcacgc gcctacccc    4680 gcgcggccac gttaactggc ggtcgccgca gcctcgggac agccggccgc gcgccgccag    4740
gctcgcggac gcgggaccac gcgccgccct ccggagggcc caagtctcga cccagccccg    4800
cgtggcgctg ggggagggggg cgcctccgcc ggaacgcggg tgggggaggg gaggggggaaa    4860 tgcgctttgt ctcgaaatgg ggcaaccgtc gccacagctc cctaccccct cgagggcaga    4920
gcagtccccc cactaactac cgggctggcc gcgcgccagg ccagccgcga ggccaccgcc    4980
cgaccctcca ctccttcccg cagctcccgg cgcggggtcc ggcagaaagg ggaggggagg    5040
ggagcggaga accgggcccc cgggacgcgt gtggcatctg aagcaccacc agcgagcgag    5100
agctagagag aaggaaagcc accgacttca ccgcctccga gctgctccgg gtcgcgggtc    5160
tgcagcgtct ccggccctcc gcgcctacag ctcaagccac atccgaaggg ggagggagcc    5220
gggagctgcg cgcggggccg ccggggggag gggtggcacc gcccacgccg ggcggccacg    5280
aagggcgggg cagcgggcgc gcgcgcggcg ggggagggg ccggcgccgc gcccgctggg    5340
aattggggcc ctaggggggag ggcggaggcg ccgacgaccg cggcacttac cgttcgcggc    5400
gtggcgcccg gtggtcccca aggggaggga aggggggaggc ggggcgagga cagtgaccgg    5460
agtctcctca gcggtggctt ttctgcttgg cagcctcagc ggctggcgcc aaaaccggac    5520
tccgcccact tcctcgcccg ccggtgcgag ggtgtggaat cctccagacg ctgggggagg    5580
gggagttggg agcttaaaaa ctagtacccc tttgggacca cttttcagcag cgaactctcc    5640 tgtacaccag gggtcagttc cacagacgcg ggccaggggt gggtcattgc ggcgtgaaca    5700
ataatttgac tagaagttga ttcgggtgtt tccggaaggg gccgagtcaa tccgccgagt    5760
tggggcacgg aaaacaaaaa gggaaggcta ctaagatttt tctggcgggg gttatcattg    5820
gcgtaactgc agggaccacc tcccgggttg aggggggctgg atctccaggc tgcggattaa    5880 gccccctcccg tcggcgttaa tttcaaactg cgcgacgttt ctcacctgcc ttcgccaagg    5940
caggggccgg gacccattc caagaggtag taactagcag gactctagcc ttccgcaatt    6000
cattgagcgc atttacggaa gtaacgtcgg gtactgtctc tggccgcaag ggtgggagga    6060
gtacgcattt ggcgtaaggt ggggcgtaga gccttccgc cattggcggc ggatagggcg    6120
tttacgcgac ggcctgacgt agcggaagac gcgttagtgg ggggaaggt tctagaaaag    6180 cggcggcagc ggctctagcg gcagtagcag cagcgccggg tcccgtgcgg aggtgctcct    6240
cgcagagttg tttctcgagc agcggcagtt ctcactacag cgccaggacg agtccggttc    6300
gtgttcgtcc gcggagatct ctctcatctc gctcggctgc gggaaatcgg gctgaagcga    6360
ctgagtccgc gatggaggta acgggtttga aatcaatgag ttattgaaaa gggcatggcg    6420
aggccgttgg cgcctcagtg gaagtcggcc agccgcctcc gtgggagaga ggcaggaaat    6480
cggaccaatt cagtagcagt ggggcttaag gtttatgaac ggggtcttga gcggaggcct    6540
gagcgtacaa acagcttccc caccctcagc ctcccggcgc catttcccttt cactgggggt    6600 gggggatggg gagctttcac atggcggacg ctgcccccgct ggggtgaaag tggggcgcgg    6660
aggcgggaat tcttattccc tttctaaagc acgctgcttc gggggccacg gcgtctcctc    6720
```

```
ggcgagcgtt tcggcgggca gcaggtcctc gtgagcgagg ctgcggagct tccccctcccc    6780 ctctctcccg ggaaccgatt tggcggccgc cattttcatg gctcgccttc ctctcagcgt    6840
tttccttata actcttttat tttcttagtg tgctttctct atcaagaagt agaagtggtt    6900
aactattttt tttttcttct cgggctgttt tcatatcgtt tcgaggtgga tttggagtgt    6960
tttgtgagct tggatcttta gagtcctgcg cacctcatta aaggcgctca gccttcccct    7020
cgatgaaatg gcgccattgc gttcggaagc cacaccgaag agcggggagg gggggtgctc    7080
cgggtttgcg ggcccggttt cagagaagat atcaccaccc agggcgtcgg gccgggttca    7140
atgcgagccg taggacaaag aaaccatttt atgttttcc tgtctttttt ttcctttgag    7200
taacggtttt atctgggtct gcagtcagta aacgacaga tgaaccgcgg caaaataaac    7260
ataaattgga agccatcggc cacgaggggc agggacgaag gtggttttct gggcggggga    7320
gggatattcg cgtcagaatc ctttactgtt cttaaggatt ccgtttaagt tgtagagctg    7380
actcatttta agtaatgttg ttactgagaa gtttaacct tacgggacag atccatggac    7440
ctttatagat gattacgagg aaagtgaaat aacgattttg tccttagtta tacttcgatt    7500
aaaacatggc ttcagaggct ccttcctgta atgcgtatgg attgatgtgc aaaactgttt    7560
tgggcctggg ccgctctgta tttgaacttt gttacttttc tcattttgtt tgcaatcttg    7620
gttgaacatt acattgataa gcataaggtc tcaagcgaag ggggtctacc tggttatttt    7680
tctttgaccc taagcacgtt tataaaataa cattgtttaa aatcgatagt ggacatcggg    7740
taagtttgga taaattgtga ggtaagtaat gagttttgc ttttttgttag tgatttgtaa    7800 aacttgttat aaatgtacat tatccgtaat ttcagtttag agataaccta tgtgctgacg    7860
acaattaaga ataaaaacta gctgaaaaaa tgaaaataac tatcgtgaca agtaaccatt    7920
tcaaaagact gctttgtgtc tcataggagc tagtttgatc atttcagtta atttttttctt    7980 taattttttac gagtcatgaa aactacagga aaaaaaatct gaactgggtt ttaccactac    8040
tttttaggag ttgggagcat gcgaatggag ggagagctcc gtagaactgg gatgagagca    8100
gcaattaatg ctgcttgcta ggaacaaaaa ataattgatt gaaaattacg tgtgactttt    8160
tagtttgcat tatgcgtttg tagcagttgg tcctggatat cactttctct cgtttgaggt    8220
tttttaacct agttaacttt taagacaggt ttccttaaca ttcataagtg cccagaatac    8280
agctgtgtag tacagcatat aaagatttca gctctgaggt ttttcctatt gacttggaaa    8340
attgttttgt gcctgtcgct tgccacatgg ccaatcaagt aagcttatcg ataccggtgg    8400
cgcgccaatt gaattaagat ctggcccaat gggccgtacg aattcgagct cggtacccgg    8460
ggatcctgat ctaatagtaa tcaattacgg ggtcattagt tcatagccca tatatggagt    8520
tccgcgttac ataacttacg gtaaatggcc cgcctggctg accgcccaac gacccccgcc    8580
cattgacgtc aataatgacg tatgttccca tagtaacgcc aatagggact ttccattgac    8640
gtcaatgggt ggagtattta cggtaaactg cccacttggc agtacatcaa gtgtatcata    8700
tgccaagtac gccccctatt gacgtcaatg acggtaaatg gcccgcctgg cattatgccc    8760
agtacatgac cttatgggac tttcctactt ggcagtacat ctacgtatta gtcatcgcta    8820
ttaccatggt gatgcggttt tggcagtaca tcaatgggcg tggatagcgg tttgactcac    8880
ggggatttcc aagtctccac cccattgacg tcaatgggag tttgttttgg caccaaaatc    8940
aacgggactt tccaaaatgt cgtaacaact ccgccccatt gacgcaaatg ggcggtaggc    9000
gtgtacggtg ggaggtctat ataagcagag ctggtttagt gaaccgtcag atccgtcgcc    9060
```

```
accatggtga gcaagggcga ggagctgttc accggggtgg tgcccatcct ggtcgagctg    9120
gacggcgacg taaacggcca caagttcagc gtgtccggcg agggcgaggg cgatgccacc    9180
tacggcaagc tgaccctgaa gttcatctgc accaccggca agctgcccgt gccctggccc    9240
accctcgtga ccaccctgac ctacggcgtg cagtgcttca gccgctaccc cgaccacatg    9300
aagcagcacg acttcttcaa gtccgccatg cccgaaggct acgtccagga gcgcaccatc    9360
ttcttcaagg acgacggcaa ctacaagacc cgcgccgagg tgaagttcga gggcgacacc    9420
ctggtgaacc gcatcgagct gaagggcatc gacttcaagg aggacggcaa catcctgggg    9480
cacaagctgg agtacaacta caacagccac aacgtctata tcatggccga caagcagaag    9540
aacggcatca aggtgaactt caagatccgc cacaacatcg aggacggcag cgtgcagctc    9600
gccgaccact accagcagaa cacccccatc ggcgacggcc ccgtgctgct gcccgacaac    9660
cactacctga gcacccagtc cgccctgagc aaagacccca acgagaagcg cgatcacatg    9720
gtcctgctgg agttcgtgac cgccgccggg atcactctcg gcatgacga gctgtacaag    9780
taaagcggcc gcgactctag atcataatca gccataccac atttgtagag gttttacttg    9840
cttaaaaaa cctcccacac ctcccccctga acctgaaaca taaaatgaat gcaattgttg    9900
ttgttaactt gtttattgca gcttataatg gttacaaata aagcaatagc atcacaaatt    9960
tcacaaataa agcattttt tcactgcatt ctagttgtgg tttgtccaaa ctcatcaatg   10020
tatcttaact agagtcgacc tgcaggcatg caagcttacc ggtggcgcgc caattgttaa   10080
ttaagatctg gcccaatggg ccgtacgaat tccttaggct accgggtagg ggaggcgctt   10140
tcccaaggc agtctggagc atgcgcttta gcagcccccgc tgggcacttg gcgctacaca   10200
agtggcctct ggcctcgcac acattccaca tccaccggcc ggtaggcgcc aaccggctcc   10260
gttctttggt ggccccttcg cgccaccttc tactcctccc ctagtcagga agttcccccc   10320
cgccccgcag ctcgcgtcgt gcaggacgtg acaaatggaa gtagcacgtc tcactagtct   10380
cgtgcagatg gacagcaccg ctgagcaatg gaagcgggta ggcctttggg gcagcggcca   10440
atagcagctt tgctccttcg ctttctgggc tcagaggctg ggaaggggtg gtccgggggg   10500
cgggctcagg ggcgggctca ggggcggggc gggcgcccga aggtcctccg gaggcccggc   10560
attctgcacg cttcaaaagc gcacgtctgc cgcgctgttc tcctcttcct catctccggg   10620
cctttcgacc agcttaccat gaccgagtac aagcccacgg tgcgcctcgc cacccgcgac   10680
gacgtcccca gggccgtacg caccctcgcc gccgcgttcg ccgactaccc cgccacgcgc   10740
cacaccgtcg atccggaccg ccacatcgag cgggtcaccg agctgcaaga actcttcctc   10800
acgcgcgtcg gctcgacat cggcaaggtg tgggtcgcgg acgacggcgc cgcggtggcg   10860
gtctggacca cgccggagag cgtcgaagcg ggggcggtgt tcgccgagat cggcccgcgc   10920
atggccgagt tgagcggttc ccggctggcg gcgcagcaac agatggaagg cctcctggcg   10980
ccgcaccggc ccaaggagcc gcgtggttc ctggccaccg tcggcgtctc gcccgaccac   11040
cagggcaagg gtctgggcag cgccgtcgtg ctccccggag tggaggcggc cgagcgcgcc   11100
ggggtgcccg ccttcctgga gacctccgcg ccccgcaacc tccccttcta cgagcggctc   11160
ggcttcaccg tcaccgccga cgtcgaggtg cccgaaggac cgcgcacctg gtgcatgacc   11220
cgcaagcccg tgcctgacg cccgcccac gacccgcagc gcccgaccga aaggagcgca   11280
cgaccccatg catccgtagac gaaatgaccg accaagcgac gcccaacctg ccatcacgag   11340
atttcgattc caccgccgcc ttctatgaaa ggttgggctt cggaatcgtt ttccgggacg   11400
ccggctggat gatcctccag cgcggggatc tcatgctgga gttcttcgcc cacccctaggg   11460
```

```
ggaggctaac tgaaacacgg aaggagacaa taccggaagg aacccgcgct atgacggcaa    11520
taaaaagaca gaataaaacg cacggtgttg ggtcgtttgt tcataaacgc ggggttcggt    11580 cccaggctg gcactctgtc gatacccac cgagacccca ttggggccaa tacgcccgcg     11640
tttcttcctt ttccccaccc cacccccaa gttcgggtga aggcccaggg ctcgcagcca    11700 acgtcgggc ggcaggcccc cagcttttgt tccctttagt gagggttaat ttcgagcttg    11760
gcgtaatcat ggtcatagct gtttcctgtg tgaaattgtt atccgctcac aattccacac    11820
aacatacgag ccggaagcat aaagtgtaaa gcctggggtg cctaatgagt gagctaactc    11880
acattaattg cgttgcgctc actgcccgct ttccagtcgg gaaacctgtc gtgccagcat    11940
cgcgagcact tttcggggaa atgtgcgcgg aaccctatt tgtttatttt tctaaataca    12000
ttcaaatatg tatccgctca tgagacaata accctgataa atgcttcaat aatattgaaa    12060
aaggaagagt atgagtattc aacatttccg tgtcgccctt attccctttt ttgcggcatt    12120
ttgccttcct gtttttgctc acccagaaac gctggtgaaa gtaaagatg ctgaagatca     12180 gttgggtgca cgagtgggtt acatcgaact ggatctcaac agcggtaaga tccttgagag    12240
ttttcgcccc gaagaacgtt ttccaatgat gagcactttt aaagttctgc tatgtggcgc    12300
ggtattatcc cgtattgacg ccgggcaaga gcaactcggt cgccgcatac actattctca    12360
gaatgacttg gttgagtact caccagtcac agaaaagcat cttacggatg gcatgacagt    12420
aagagaatta tgcagtgctg ccataaccat gagtgataac actgcggcca acttacttct    12480
gacaacgatc ggaggaccga aggagctaac cgcttttttg cacaacatgg gggatcatgt    12540
aactcgcctt gatcgttggg aaccggagct gaatgaagcc ataccaaacg acgagcgtga    12600
caccacgatg cctgtagcaa tggcaacaac gttgcgcaaa ctattaactg gcgaactact    12660
tactctagct tcccggcaac aattaataga ctggatggag gcggataaag ttgcaggacc    12720
acttctgcgc tcggcccttc cggctggctg gtttattgct gataaatctg gagccggtga    12780
gcgtgggtct cgcggtatca ttgcagcact ggggccagat ggtaagccct cccgtatcgt    12840
agttatctac acgacgggga gtcaggcaac tatggatgaa cgaaatagac agatcgctga    12900
gataggtgcc tcactgatta agcattggta actgtcagac tcgcgacact gcattaatga    12960
atcggccaac gcgcggggag aggcggtttg cgtattgggc gctcttccgc ttcctcgctc    13020
actgactcgc tgcgctcggt cgttcggctg cggcgagcgg tatcagctca ctcaaaggcg    13080
gtaatacggt tatccacaga atcaggggat aacgcaggaa agaacatgtg agcaaaaggc    13140
cagcaaaagg ccaggaaccg taaaaaggcc gcgttgctgg cgttttttcca taggctccgc    13200 cccctgacg agcatcacaa aaatcgacgc tcaagtcaga ggtggcgaaa cccgacagga    13260
ctataaagat accaggcgtt tccccctgga agctccctcg tgcgctctcc tgttccgacc    13320
ctgccgctta ccggatacct gtccgccttt ctcccttcgg gaagcgtggc gctttctcat    13380
agctcacgct gtaggtatct cagttcggtg taggtcgttc gctccaagct gggctgtgtg    13440
cacgaacccc ccgttcagcc cgaccgctgc gccttatccg gtaactatcg tcttgagtcc    13500
aacccggtaa gacacgactt atcgccactg gcagcagcca ctggtaacag gattagcaga    13560
gcgaggtatg taggcggtgc tacagagttc ttgaagtggt ggcctaacta cggctacact    13620
agaaggacag tatttggtat ctgcgctctg ctgaagccag ttaccttcgg aaaaagagtt    13680
ggtagctctt gatccggcaa acaaaccacc gctggtagcg gtggtttttt tgtttgcaag    13740
cagcagatta cgcgcagaaa aaaaggatct caagaagatc ctttgatctt ttctacgggg    13800
```

-continued

| | |
|---|---|
| tctgacgctc agtggaacga aaactca | 13827 |

<210> SEQ ID NO 19
<211> LENGTH: 8585
<212> TYPE: DNA
<213> ORGANISM: Artificial
<220> FEATURE:
<223> OTHER INFORMATION: Vector pRPS11 1005 EGFP

<400> SEQUENCE: 19

| | |
|---|---|
| cgttgtaaaa cgacggccag tgaattgtaa tacgactcac tatagggcga attgggtacc | 60 |
| gggccccccc tcgaagttta attcgccctt aagactgttt gcctcatgcc tgcctggcct | 120 |
| gcccttcctc cgccgccaac tagggaagtg gggaccaaag gttccttagg cactgctcct | 180 |
| gtgggtagag gggacattag agagctgaca gcgcaccacc tgcatgagtt tttattaaag | 240 |
| tgcaaaccat gggatgaatc agttgagctt cagtgttgaa aatgagtagc agggctgccc | 300 |
| cacccacctg accaagtacc ctattctgca gctatgaaaa tgagatctgc acatgagctg | 360 |
| gggttcacaa gtgcacactt ggagcactgc cttgctcctt cccagcagac cacaaagcag | 420 |
| tatttttctg gaggatttta tgtgctaata aattatttga cttaagtgtg tacgatgtgt | 480 |
| gctgtgcaga gaggggcaga gggcaccagc aggtcatctg catgggggc cctttgggt | 540 |
| gaatccttgc tcacgggata ggctttgttg ctcaaaagtt gcagatatac atcttgggtc | 600 |
| ctgtcctaga tggtgttact gtaagtcagc accaagatac aagagctggt acctggactg | 660 |
| taggaggtca ggccatgaca caaaggctgg gactaaaggc atttaccacg cctgagtctt | 720 |
| ctggttcttt aaacatcaaa tccttccggg gctggcgag atggctcagt ggttaagagc | 780 |
| acagactgct cttacgaagg atccgagttc aaatcccagc aaccaaatgg tgcctaacaa | 840 |
| ctatccataa tgaaatctga tgccctcttc tggagtatct gagaacagct acagtgtact | 900 |
| tacatataat cttaaaaatg cttcccatgt taaccaccac tagagttttt attacagcta | 960 |
| gctgacctgg aagccaagtc cttatgcctc cgtgagtgct ggggttaaaa agatccagca | 1020 |
| ccactcaaaa tgtcaatcta ttttgaaaat atgctttata ctgttctagc ccatctgtgc | 1080 |
| agggctagaa cggtgaatac gagaaactga cacaagcttt tgccacctgg ctaaatggtt | 1140 |
| cctctattac ctggggtggt cacctaaggt tagacactca tccacgagta gtcaggacat | 1200 |
| aaacccatca aagtgtgggt agacgcgcag cctgagatac tgtcaacaaa ggacatgcga | 1260 |
| ccttggtgac gtcggccttt aataaaagga agaaaggttg actattcggt cgacgctggc | 1320 |
| tgctcctgac atcgtatggc agatactctg ctgtaaagcg gttcacccct tcttgagac | 1380 |
| ccgctctgca cggccgcttc tctctggaaa ctgaatccca gcacgtgttt cccaacccgt | 1440 |
| acggcacgcc ttctccgccc taagcctcgc cgtaccacat gatgcacgtt tcctccacat | 1500 |
| cgtgctcctg aaatctcgcg agatgatagg atcttcccgc cccttagtcc tcccccgtca | 1560 |
| tggcggcgta cggacagtcc caggaacgcg ggctctcgcc ggaagtacct cccacctccg | 1620 |
| tgaggataac cccgcgtcac ttccgccccg acctcgcgtg gtgaataagg aagccgggag | 1680 |
| cggccctgcc tctcccttc tccggcgcc gggaagatgg cggacattca ggttcgagcg | 1740 |
| tttagttgct ttcccccgac gcttcggtgt ggagcgtatc ccttggcgtc tcgttgtct | 1800 |
| tacgcattag ctgaagcgag gatgcctgcg aatgccttcg tctcaggcgg ctcggaaatc | 1860 |
| cgggctctac gcagtaatgg ggtccctggc gcttcgggag ttggttctta aagctcagag | 1920 |
| cttaacgggt gagggattgt ggcgggagga gggcatcctg cggcgcggga gtcctgcggc | 1980 |
| ggcagagccg gggacactgg gtaaagcagg tttttttccc ttgatggaga ctgaggcccg | 2040 |

```
gacctcgtgc gctctacggc agggctgcgg tcccgacctc gctgtagttt tcagtgtgag    2100
cgcagctctg gcctcgatga gcttaggctt gtcttaaact tgccatcctg cctcaacctc    2160
aaccgggatg acagatccgg cccaccaggc tcggctacgt ggacataagc ttgaatcccg    2220
aatgagtgga tttgtatgtt ttggaggtcc agtctggctg aaaagctctt tttgatctca    2280
gccgtgagtt ctgcaggctg tggaggtgtt agatgggacg cagtgtgtga gctaaactag    2340
acttggggtg gttggagagc cctgaccagc cggttttggc gattggggca aataaggttg    2400
aaggtaggaa ggaagaaata ttgtctctga tttccttgaa ctttacctgc aacctcacca    2460
aattctcatc cctacagacg gagcgtgctt accaaaagca gcctacgatc tttcaaaaca    2520
agaagcgggt tctgctggga gaaaccggca aggaaaaact ccctcggtac tacaagaata    2580
tcggtctagg cttcaagacg cctaaagagg tacaggaccc tccagcagat gagatccctg    2640
ctgccctgca cgtgtgggag cacagccacc ccgccccctt cacagtggct cccatgggc    2700 ccctgggaat tgtagtatgg gccctgaggc gtcatccttg gttctgttta ggaagtggta    2760
atctaaaccc cactttctta actttgcagg ctattgaggg tacctacata gacaagaaat    2820
gccccttcac tggtaacgtc tccatccgag gtcggatcct gtctggtgag tgggatgttg    2880
gaagggtggt tctaggttcc tgcgtccagg ggcgctggca agtgatgtct gttctcacga    2940
tggtcttcag atgtcctcta gggcactgct gagacagcca gttgacaaag ctgatgccat    3000
aaatggagct tcttgggagc cccgttcaac tgactcctac ctgctaacac ctttctgtta    3060
ctctcccagg tgtcgtgacg aagatgaaga tgcagaggac cattgtcatc caagggcgaa    3120
acatttaaat ctagaagctt atcgataccg gtggcgcgcc aattgaatta agatctggcc    3180
caatgggccg tacgaattcg agctcggtac ccggggatcc tgatctaata gtaatcaatt    3240
acggggtcat tagttcatag cccatatatg gagttccgcg ttacataact acggtaaat    3300 ggcccgcctg gctgaccgcc caacgacccc cgcccattga cgtcaataat gacgtatgtt    3360
cccatagtaa cgccaatagg gactttccat tgacgtcaat gggtggagta tttacggtaa    3420
actgcccact tggcagtaca tcaagtgtat catatgccaa gtacgccccc tattgacgtc    3480
aatgacggta aatggcccgc ctggcattat gcccagtaca tgaccttatg gactttcct    3540 acttggcagt acatctacgt attagtcatc gctattacca tggtgatgcg gttttggcag    3600
tacatcaatg ggcgtggata gcggtttgac tcacgggat ttccaagtct caccccatt    3660 gacgtcaatg ggagtttgtt ttggcaccaa aatcaacggg actttccaaa atgtcgtaac    3720
aactccgccc cattgacgca aatgggcggt aggcgtgtac ggtgggaggt ctatataagc    3780
agagctggtt tagtgaaccg tcagatccgt cgccaccatg gtgagcaagg gcgaggagct    3840
gttcaccggg gtggtgccca tcctggtcga gctggacggc gacgtaaacg gccacaagtt    3900
cagcgtgtcc ggcgagggcg agggcgatgc cacctacggc aagctgaccc tgaagttcat    3960
ctgcaccacc ggcaagctgc ccgtgccctg gcccaccctc gtgaccaccc tgacctacgg    4020
cgtgcagtgc ttcagccgct accccgacca catgaagcag cacgacttct tcaagtccgc    4080
catgcccgaa ggctacgtcc aggagcgcac catcttcttc aaggacgacg gcaactacaa    4140
gacccgcgcc gaggtgaagt tcgagggcga caccctggtg aaccgcatcg agctgaaggg    4200
catcgacttc aaggaggacg gcaacatcct ggggcacaag ctggagtaca actacaacag    4260
ccacaacgtc tatatcatgg ccgacaagca gaagaacggc atcaaggtga acttcaagat    4320
ccgccacaac atcgaggacg gcagcgtgca gctcgccgac cactaccagc agaacacccc    4380
```

```
catcggcgac ggccccgtgc tgctgcccga caaccactac ctgagcaccc agtccgccct    4440
gagcaaagac cccaacgaga agcgcgatca catggtcctg ctggagttcg tgaccgccgc    4500
cgggatcact ctcggcatgg acgagctgta caagtaaagc ggccgcgact ctagatcata    4560
atcagccata ccacatttgt agaggtttta cttgctttaa aaaacctccc acacctcccc    4620
ctgaacctga aacataaaat gaatgcaatt gttgttgtta acttgtttat tgcagcttat    4680
aatggttaca aataaagcaa tagcatcaca aatttcacaa ataaagcatt tttttcactg    4740
cattctagtt gtggtttgtc caaactcatc aatgtatctt aactagagtc gacctgcagg    4800
catgcaagct taccggtggc gcgcgcgcca attgttaatt aagatctggc caatgggcc     4860 gtacgaattc cttaggctac cgggtagggg aggcgctttt cccaaggcag tctggagcat    4920
gcgctttagc agccccgctg ggcacttggc gctacacaag tggcctctgg cctcgcacac    4980
attccacatc caccggccgg taggcgccaa ccggctccgt tctttggtgg ccccttcgcg    5040
ccaccttcta ctcctcccct agtcaggaag ttcccccccg ccccgcagct cgcgtcgtgc    5100
aggacgtgac aaatggaagt agcacgtctc actagtctcg tgcagatgga cagcaccgct    5160
gagcaatgga agcgggtagg cctttggggc agcggccaat agcagctttg ctccttcgct    5220
ttctgggctc agaggctggg aaggggtggg tccggggggcg ggctcagggg cgggctcagg    5280
ggcggggcgg gcgcccgaag gtcctccgga ggcccggcat tctgcacgct tcaaaagcgc    5340
acgtctgccg cgctgttctc ctcttcctca tctccgggcc tttcgaccag cttaccatga    5400
ccgagtacaa gcccacggtg cgcctcgcca ccgcgacga cgtccccagg gccgtacgca    5460
ccctcgccgc cgcgttcgcc gactaccccg ccacgcgcca caccgtcgat ccggaccgcc    5520
acatcgagcg ggtcaccgag ctgcaagaac tcttcctcac gcgcgtcggg ctcgacatcg    5580
gcaaggtgtg ggtcgcggac gacggcgccg cggtggcggt ctggaccacg ccggagagcg    5640
tcgaagcggg ggcggtgttc gccgagatcg gcccgcgcat ggccgagttg agcggttccc    5700
ggctggccgc gcagcaacag atggaaggcc tcctggcgcc gcaccggccc aaggagcccg    5760
cgtggttcct ggccaccgtc ggcgtctcgc ccgaccacca gggcaagggt ctgggcagcg    5820
ccgtcgtgct ccccggagtg gaggcggccg agcgcgccgg ggtgcccgcc ttcctggaga    5880
cctccgcgcc ccgcaacctc cccttctacg agcggctcgg cttcaccgtc accgccgacg    5940
tcgaggtgcc cgaaggaccg cgcacctggt gcatgacccg caagcccggt gcctgacgcc    6000
cgccccacga cccgcagcgc ccgaccgaaa ggagcgcacg accccatgca tcgtagacga    6060
aatgaccgac caagcgacgc ccaacctgcc atcacgagat ttcgattcca ccgccgcctt    6120
ctatgaaagg ttgggcttcg gaatcgtttt ccgggacgcc ggctggatga tcctccagcg    6180
cggggatctc atgctggagt tcttcgccca ccctagggggg aggctaactg aaacacggaa    6240
ggagacaata ccggaaggaa cccgcgctat gacggcaata aaaagacaga ataaaacgca    6300
cggtgttggg tcgtttgttc ataaacgcgg ggttcggtcc cagggctggc actctgtcga    6360
taccccaccg agaccccatt ggggccaata cgcccgcgtt tcttcctttt ccccacccca    6420
ccccccaagt tcgggtgaag gcccagggct cgcagccaac gtcggggcgg caggcccca     6480 gcttttgttc cctttagtga gggttaattt cgagcttggc gtaatcatgg tcatagctgt    6540
ttcctgtgtg aaattgttat ccgctcacaa ttccacacaa catacgagcc ggaagcataa    6600
agtgtaaagc ctggggtgcc taatgagtga gctaactcac attaattgcg ttgcgctcac    6660
tgcccgcttt ccagtcggga aacctgtcgt gccagcatcg cgagcacttt tcggggaaat    6720
gtgcgcggaa cccctatttg tttatttttc taaatacatt caaatatgta tccgctcatg    6780
```

```
agacaataac cctgataaat gcttcaataa tattgaaaaa ggaagagtat gagtattcaa      6840
catttccgtg tcgcccttat tcccttttt gcggcatttt gccttcctgt ttttgctcac      6900
ccagaaacgc tggtgaaagt aaaagatgct gaagatcagt tgggtgcacg agtgggttac      6960
atcgaactgg atctcaacag cggtaagatc cttgagagtt ttcgccccga agaacgtttt      7020
ccaatgatga gcacttttaa agttctgcta tgtggcgcgg tattatcccg tattgacgcc      7080
gggcaagagc aactcggtcg ccgcatacac tattctcaga atgacttggt tgagtactca      7140
ccagtcacag aaaagcatct tacggatggc atgacagtaa gagaattatg cagtgctgcc      7200
ataaccatga gtgataacac tgcggccaac ttacttctga caacgatcgg aggaccgaag      7260
gagctaaccg cttttttgca acatggggat catgtaa ctcgccttga tcgttgggaa       7320
ccggagctga atgaagccat accaaacgac gagcgtgaca ccacgatgcc tgtagcaatg      7380
gcaacaacgt tgcgcaaact attaactggc gaactactta ctctagcttc ccggcaacaa      7440
ttaatagact ggatggaggc ggataaagtt gcaggaccac ttctgcgctc ggcccttccg      7500
gctggctggt ttattgctga taaatctgga gccggtgagc gtgggtctcg cggtatcatt      7560
gcagcactgg ggccagatgg taagccctcc cgtatcgtag ttatctacac gacggggagt      7620
caggcaacta tggatgaacg aaatagacag atcgctgaga taggtgcctc actgattaag      7680
cattggtaac tgtcagactc gcgacactgc attaatgaat cggccaacgc gcggggagag      7740
gcggtttgcg tattgggcgc tcttccgctt cctcgctcac tgactcgctg cgctcggtcg      7800
ttcggctgcg gcgagcggta tcagctcact caaaggcggt aatacggtta tccacagaat      7860
caggggataa cgcaggaaag aacatgtgag caaaaggcca gcaaaaggcc aggaaccgta      7920
aaaaggccgc gttgctggcg tttttccata ggctccgccc ccctgacgag catcacaaaa      7980
atcgacgctc aagtcagagg tggcgaaacc cgacaggact ataaagatac caggcgtttc      8040
cccctggaag ctccctcgtg cgctctcctg ttccgaccct gccgcttacc ggatacctgt      8100
ccgcctttct cccttcggga agcgtggcgc tttctcatag ctcacgctgt aggtatctca      8160
gttcggtgta ggtcgttcgc tccaagctgg gctgtgtgca cgaaccccc gttcagcccg       8220 accgctgcgc cttatccggt aactatcgtc ttgagtccaa cccggtaaga cacgacttat      8280
cgccactggc agcagccact ggtaacagga ttagcagagc gaggtatgta ggcggtgcta      8340
cagagttctt gaagtggtgg cctaactacg gctacactag aaggacagta tttggtatct      8400
gcgctctgct gaagccagtt accttcggaa aaagagttgg tagctcttga tccggcaaac      8460
aaaccaccgc tggtagcggt ggtttttttg tttgcaagca gcagattacg cgcagaaaaa      8520
aaggatctca agaagatcct ttgatctttt ctacggggtc tgacgctcag tggaacgaaa      8580
actca                                                                 8585

<210> SEQ ID NO 20
<211> LENGTH: 5546
<212> TYPE: DNA
<213> ORGANISM: Artificial
<220> FEATURE:
<223> OTHER INFORMATION: Vector pCET 1005 EGFP

<400> SEQUENCE: 20
cgttgtaaaa cgacggccag tgaattgtaa tacgactcac tatagggcga attgggtacc        60
gggccccccc tcgaagttta acatttaaa tctagaagct tatcgatacc ggtggcgcgc       120
caattgaatt aagatctggc ccaatgggcc gtacgaattc gagctcggta cccgggggatc      180
```

```
ctgatctaat agtaatcaat tacggggtca ttagttcata gcccatatat ggagttccgc   240
gttacataac ttacggtaaa tggcccgcct ggctgaccgc ccaacgaccc ccgcccattg   300
acgtcaataa tgacgtatgt tcccatagta acgccaatag ggactttcca ttgacgtcaa   360
tgggtggagt atttacggta aactgcccac ttggcagtac atcaagtgta tcatatgcca   420
agtacgcccc ctattgacgt caatgacggt aaatggcccg cctggcatta tgcccagtac   480
atgaccttat gggactttcc tacttggcag tacatctacg tattagtcat cgctattacc   540
atggtgatgc ggttttggca gtacatcaat gggcgtggat agcggtttga ctcacgggga   600
tttccaagtc tccaccccat tgacgtcaat gggagtttgt tttggcacca aaatcaacgg   660
gactttccaa aatgtcgtaa caactccgcc ccattgacgc aaatgggcgg taggcgtgta   720
cggtgggagg tctatataag cagagctggt ttagtgaacc gtcagatccg tcgccaccat   780
ggtgagcaag ggcgaggagc tgttcaccgg ggtggtgccc atcctggtcg agctggacgg   840
cgacgtaaac ggccacaagt tcagcgtgtc cggcgagggc gagggcgatg ccacctacgg   900
caagctgacc ctgaagttca tctgcaccac cggcaagctg cccgtgccct ggcccaccct   960
cgtgaccacc ctgacctacg gcgtgcagtg cttcagccgc taccccgacc acatgaagca  1020
gcacgacttc ttcaagtccg ccatgcccga aggctacgtc caggagcgca ccatcttctt  1080
caaggacgac ggcaactaca agacccgcgc cgaggtgaag ttcgagggcg acaccctggt  1140
gaaccgcatc gagctgaagg gcatcgactt caaggaggac ggcaacatcc tggggcacaa  1200
gctggagtac aactacaaca gccacaacgt ctatatcatg gccgacaagc agaagaacgg  1260
catcaaggtg aacttcaaga tccgccacaa catcgaggac ggcagcgtgc agctcgccga  1320
ccactaccag cagaacaccc ccatcggcga cggccccgtg ctgctgcccg acaaccacta  1380
cctgagcacc cagtccgccc tgagcaaaga ccccaacgag aagcgcgatc acatggtcct  1440
gctggagttc gtgaccgccg ccgggatcac tctcggcatg gacgagctgt acaagtaaag  1500
cggccgcgac tctagatcat aatcagccat accacatttg tagaggtttt acttgcttta  1560
aaaaacctcc cacacctccc cctgaacctg aaacataaaa tgaatgcaat tgttgttgtt  1620
aacttgttta ttgcagctta taatggttac aaataaagca atagcatcac aaatttcaca  1680
aataaagcat ttttttcact gcattctagt tgtggtttgt ccaaactcat caatgtatct  1740
taactagagt cgacctgcag gcatgcaagc ttaccggtgg cgcgcgcgcc aattgttaat  1800
taagatctgg cccaatgggc cgtacgaatt ccttaggcta ccgggtaggg gaggcgcttt  1860
tcccaaggca gtctggagca tgcgctttag cagccccgct gggcacttgg cgctacacaa  1920
gtggcctctg gcctcgcaca cattccacat ccaccggccg gtaggcgcca accggctccg  1980
ttctttggtg gccccttcgc gccaccttct actcctcccc tagtcaggaa gttcccccc   2040
gccccgcagc tcgcgtcgtg caggacgtga caaatggaag tagcacgtct cactagtctc  2100
gtgcagatgg acagcaccgc tgagcaatgg aagcgggtag cctttgggg cagcggccaa  2160
tagcagcttt gctccttcgc tttctgggct cagaggctgg aaggggtgg gtccgggggc  2220
gggctcaggg gcgggctcag gggcggggcg gcgcccgaa ggtcctccgg aggcccggca  2280
ttctgcacgc ttcaaaagcg cacgtctgcc gcgctgttct cctcttcctc atctccgggc  2340
ctttcgacca gcttaccatg accgagtaca agcccacggt gcgcctcgcc acccgcgacg  2400
acgtccccag ggccgtacgc accctcgccg ccgcgttcgc cgactacccc gccacgcgcc  2460
acaccgtcga tccggaccgc cacatcgagc gggtcaccga gctgcaagaa ctcttcctca  2520
cgcgcgtcgg gctcgacatc ggcaaggtgt gggtcgcgga cgacggcgcc gcggtggcgg  2580
```

-continued

```
tctggaccac gccggagagc gtcgaagcgg gggcggtgtt cgccgagatc ggcccgcgca    2640
tggccgagtt gagcggttcc cggctggccg cgcagcaaca gatggaaggc ctcctggcgc    2700
cgcaccggcc caaggagccc gcgtggttcc tggccaccgt cggcgtctcg cccgaccacc    2760
agggcaaggg tctgggcagc gccgtcgtgc tccccggagt ggaggcggcc gagcgcgccg    2820
gggtgcccgc cttcctggag acctccgcgc cccgcaacct ccccttctac gagcggctcg    2880
gcttcaccgt caccgccgac gtcgaggtgc ccgaaggacc gcgcacctgg tgcatgaccc    2940
gcaagcccgg tgcctgacgc ccgccccacg acccgcagcg cccgaccgaa aggagcgcac    3000
gaccccatgc atcgtagacg aaatgaccga ccaagcgacg cccaacctgc catcacgaga    3060
tttcgattcc accgccgcct tctatgaaag gttgggcttc ggaatcgttt tccgggacgc    3120
cggctggatg atcctccagc gcggggatct catgctggag ttcttcgccc accctagggg    3180
gaggctaact gaaacacgga aggagacaat accggaagga acccgcgcta tgacggcaat    3240
aaaaagacag aataaaacgc acggtgttgg gtcgtttgtt cataaacgcg gggttcggtc    3300
ccagggctgg cactctgtcg ataccccacc gagaccccat tggggccaat acgcccgcgt    3360
ttcttccttt tccccacccc acccccaag ttcgggtgaa ggcccagggc tcgcagccaa    3420
cgtcggggcg gcaggccccc agcttttgtt ccctttagtg agggttaatt tcgagcttgg    3480
cgtaatcatg gtcatagctg tttcctgtgt gaaattgtta tccgctcaca attccacaca    3540
acatacgagc cggaagcata agtgtaaag cctggggtgc ctaatgagtg agctaactca    3600
cattaattgc gttgcgctca ctgcccgctt tccagtcggg aaacctgtcg tgccagcatc    3660
gcgagcactt ttcggggaaa tgtgcgcgga acccctattt gtttattttt ctaaatacat    3720
tcaaatatgt atccgctcat gagacaataa ccctgataaa tgcttcaata atattgaaaa    3780
aggaagagta tgagtattca actttccgt gtcgccctta ttcccttttt tgcggcattt    3840
tgccttcctg ttttgctca cccagaaacg ctggtgaaag taaaagatgc tgaagatcag    3900
ttgggtgcac gagtgggtta catcgaactg gatctcaaca gcggtaagat ccttgagagt    3960
tttcgccccg aagaacgttt tccaatgatg agcacttta aagttctgct atgtggcgcg    4020
gtattatccc gtattgacgc cgggcaagag caactcggtc gccgcataca ctattctcag    4080
aatgacttgg ttgagtactc accagtcaca gaaaagcatc ttacgatgg catgacagta    4140 agagaattat gcagtgctgc cataaccatg agtgataaca ctgcggccaa cttacttctg    4200
acaacgatcg aggaccgaa ggagctaacc gcttttttgc acaacatggg gatcatgta    4260 actcgccttg atcgttggga accggagctg aatgaagcca taccaaacga cgagcgtgac    4320
accacgatgc ctgtagcaat ggcaacaacg ttgcgcaaac tattaactgg cgaactactt    4380
actctagctt cccggcaaca attaatagac tggatggagg cggataaagt tgcaggacca    4440
cttctgcgct cggcccttcc ggctggctgg tttattgctg ataaatctgg agccggtgag    4500
cgtgggtctc gcggtatcat tgcagcactg gggccagatg gtaagccctc ccgtatcgta    4560
gttatctaca cgacggggag tcaggcaact atggatgaac gaaatagaca gatcgctgag    4620
ataggtgcct cactgattaa gcattggtaa ctgtcagact gcgacactg cattaatgaa    4680 tcggccaacg cgcggggaga ggcggtttgc gtattgggcg ctcttccgct tcctcgctca    4740
ctgactcgct gcgctcggtc gttcggctgc ggcgagcggt atcagctcac tcaaaggcgg    4800
taatacggtt atccacagaa tcaggggata acgcaggaaa gaacatgtga gcaaaaggcc    4860
agcaaaaggc caggaaccgt aaaaaggccg cgttgctggc gttttccat aggctccgcc    4920
```

-continued

```
ccoctgacga gcatcacaaa aatcgacgct caagtcagag gtggcgaaac ccgacaggac    4980
tataaagata ccaggcgttt cccctggaa gctccctcgt gcgctctcct gttccgaccc     5040
tgccgcttac cggatacctg tccgcctttc tccttcggg aagcgtggcg ctttctcata     5100
gctcacgctg taggtatctc agttcggtgt aggtcgttcg ctccaagctg ggctgtgtgc    5160 acgaacccc cgttcagccc gaccgctgcg ccttatccgg taactatcgt cttgagtcca    5220
acccggtaag acacgactta tcgccactgg cagcagccac tggtaacagg attagcagag    5280
cgaggtatgt aggcggtgct acagagttct tgaagtggtg gcctaactac ggctacacta    5340
gaaggacagt atttggtatc tgcgctctgc tgaagccagt taccttcgga aaaagagttg    5400
gtagctcttg atccggcaaa caaaccaccg ctggtagcgg tggttttttt gtttgcaagc    5460
agcagattac gcgcagaaaa aaaggatctc aagaagatcc tttgatcttt tctacggggt    5520
ctgacgctca gtggaacgaa aactca                                         5546
```